(12) United States Patent
Weaver et al.

(10) Patent No.: US 11,565,031 B2
(45) Date of Patent: *Jan. 31, 2023

(54) MEDICAL WETNESS SENSING DEVICES AND RELATED SYSTEMS AND METHODS

(71) Applicant: Fresenius Medical Care Holdings, Inc., Waltham, MA (US)

(72) Inventors: Colin Weaver, Pleasanton, CA (US); Martin Joseph Crnkovich, Walnut Creek, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 647 days.

This patent is subject to a terminal disclaimer.

(21) Appl. No.: 16/559,815

(22) Filed: Sep. 4, 2019

(65) Prior Publication Data
US 2019/0388605 A1 Dec. 26, 2019

Related U.S. Application Data

(63) Continuation of application No. 15/479,777, filed on Apr. 5, 2017, now Pat. No. 10,441,705.

(51) Int. Cl.
*A61M 1/36* (2006.01)
*A61M 1/14* (2006.01)
(Continued)

(52) U.S. Cl.
CPC ..... *A61M 1/3656* (2014.02); *A61F 13/00004* (2013.01); *A61M 1/14* (2013.01);
(Continued)

(58) Field of Classification Search
CPC .... A61M 1/3656; A61M 1/3403; A61M 1/14; A61M 5/16831; A61M 2205/13;
(Continued)

(56) References Cited

U.S. PATENT DOCUMENTS 7,147,615 B2   12/2006  Wariar et al.
7,605,710 B2 * 10/2009  Crnkovich .......... A61M 1/3656
                                                     340/603
(Continued)

FOREIGN PATENT DOCUMENTS

CN    101505812 A    8/2009
CN    102098958 A    6/2011
(Continued)

OTHER PUBLICATIONS

"Patient Safety by Fresenius Medical Care; Where new benchmarks are set," Cardioprotective Hemodialysis, Fresenius Medical Care Deutschland GmbH, 2012, 20 pages.
(Continued)

*Primary Examiner* — Philip R Wiest
(74) *Attorney, Agent, or Firm* — Fish & Richardson P.C.

(57) ABSTRACT

A medical wetness sensing device includes a base adapted to be disposed on a wearer of the medical wetness sensing device. The base includes a first electrical conductor and a second electrical conductor electrically insulated from the first electrical conductor. The first electrical conductor includes a hinge portion enabling a first portion of the first electrical conductor to deflect, at the hinge portion, relative to a second portion of the first electrical conductor. The medical wetness sensing device includes a controller electrically connected to the first electrical conductor and the second electrical conductor. The controller is configured to detect a presence or an absence of a medical fluid electrically connecting the first and second electrical conductors.

26 Claims, 19 Drawing Sheets

(51) Int. Cl.
*A61M 1/34* (2006.01)
*A61F 13/00* (2006.01)
*A61M 5/168* (2006.01)
*G01M 3/16* (2006.01)

(52) U.S. Cl.
CPC ...... *A61M 1/3403* (2014.02); *A61M 5/16831* (2013.01); *G01M 3/16* (2013.01); *A61F 2013/00412* (2013.01); *A61M 2205/13* (2013.01); *A61M 2205/15* (2013.01); *A61M 2205/3317* (2013.01); *A61M 2205/3561* (2013.01); *A61M 2205/3592* (2013.01); *A61M 2205/50* (2013.01)

(58) Field of Classification Search
CPC ...... A61M 2205/15; A61M 2205/3317; A61M 2205/3561; A61M 2205/3592; A61M 2205/50; G01M 3/16
See application file for complete search history.

(56) References Cited

U.S. PATENT DOCUMENTS

| | | | |
|---|---|---|---|
| 7,973,667 | B2 | 7/2011 | Crnkovich et al. |
| 8,454,550 | B2 | 6/2013 | Koenig et al. |
| 8,818,482 | B2 | 8/2014 | Phillips et al. |
| 8,981,948 | B2 | 3/2015 | Olde et al. |
| 9,274,083 | B2 | 3/2016 | Alatainio |
| 9,629,964 | B2 | 4/2017 | Wuepper |
| 10,117,306 | B2 | 10/2018 | Yoo |
| 2002/0198483 | A1* | 12/2002 | Wariar ............. A61B 5/150961 600/372 |
| 2009/0322543 | A1 | 12/2009 | Crnkovich et al. |
| 2010/0100026 | A1 | 4/2010 | Morris |
| 2013/0150769 | A1 | 6/2013 | Heppe |
| 2014/0012197 | A1 | 1/2014 | Heppe et al. |
| 2014/0183106 | A1* | 7/2014 | Kotsos ................. G16H 40/63 210/85 |
| 2015/0374896 | A1 | 12/2015 | Du et al. |
| 2016/0166757 | A1 | 6/2016 | Koyama et al. |
| 2017/0106151 | A1 | 4/2017 | Schmidt et al. |

FOREIGN PATENT DOCUMENTS

| | | |
|---|---|---|
| CN | 102316836 A | 1/2012 |
| CN | 103137731 A | 6/2013 |
| CN | 104272076 A | 1/2015 |
| CN | 104769423 A | 7/2015 |
| CN | 204600442 U | 9/2015 |
| CN | 105845702 A | 8/2016 |
| CN | 205490321 U | 8/2016 |
| CN | 205814756 U | 12/2016 |
| CN | 106409945 A | 2/2017 |
| DE | 102010024654 | 12/2011 |
| JP | 2015-167697 A | 9/2015 |
| WO | WO 1999/026686 | 6/1999 |

OTHER PUBLICATIONS

International Search Report and Written Opinion in International Application No. PCT/US2018/025037, dated Jun. 21, 2018, 16 pages.
International Preliminary Report on Patentability in Application No. PCT/US2018/02037, dated Oct. 8, 2019, 9 pages.

* cited by examiner

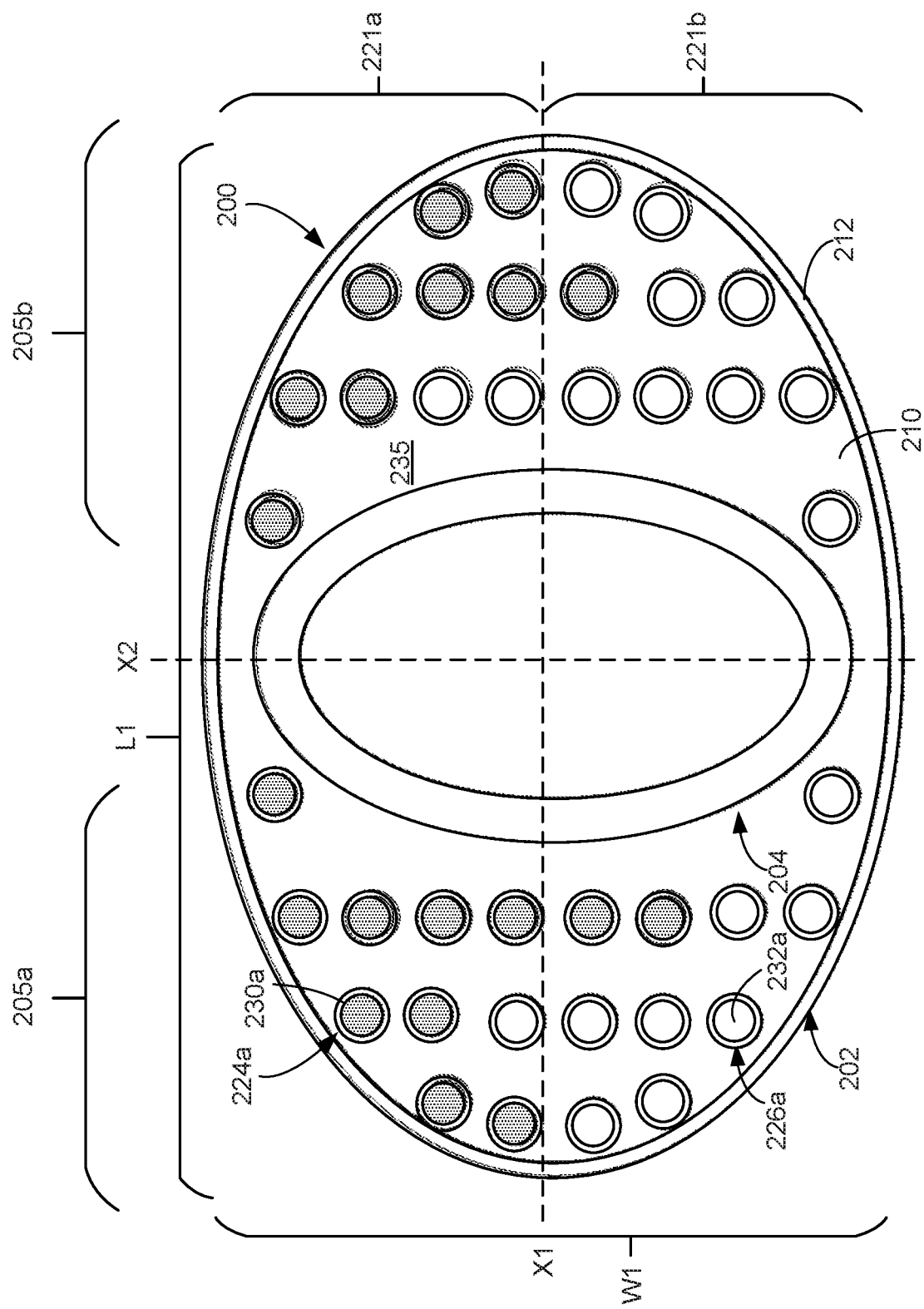

MEDICAL WETNESS SENSING DEVICES AND RELATED SYSTEMS AND METHODS

CROSS-REFERENCE TO RELATED APPLICATIONS

This application is a continuation application under 35 USC § 120 of and claims priority to U.S. application Ser. No. 15/479,777, filed on Apr. 5, 2017.

TECHNICAL FIELD

This disclosure relates to systems and devices for sensing wetness, in particular, to systems and devices for sensing wetness during a dialysis treatment.

BACKGROUND

During dialysis treatment, arterial and venous access needles are typically inserted into a patient such that blood can be drawn from the patient through the arterial access needle, flown through a dialyzer to filter the blood, and then returned to the patient through the venous access needle. In some cases, the venous access needle may become dislodged. In the case that such an event goes unnoticed, an arterial access needle can continue to draw blood from the patient while the dislodged venous access needle does not return blood to the patient.

SUMMARY

In one aspect, a medical wetness sensing device includes a base adapted to be disposed on a wearer of the medical wetness sensing device. The base includes a first electrical conductor and a second electrical conductor electrically insulated from the first electrical conductor. The first electrical conductor includes a hinge portion enabling a first portion of the first electrical conductor to deflect, at the hinge portion, relative to a second portion of the first electrical conductor. The medical wetness sensing device includes a controller electrically connected to the first electrical conductor and the second electrical conductor. The controller is configured to detect a presence or an absence of a medical fluid electrically connecting the first and second electrical conductors.

In another aspect, a dialysis system includes a dialysis machine, a medical wetness sensing device, and a wireless transmitter. The dialysis machine includes a wireless receiver. The medical wetness sensing device includes a base including first and second electrical conductors configured to be electrically connected to one another when a medical fluid is present on a surface of the base to be disposed on a wearer of the medical wetness sensing device. The first electrical conductor includes a hinge portion to enable a first portion of the first electrical conductor to deflect, at the hinge portion, relative to a second portion of the first electrical conductor. The medical wetness sensing device includes a controller to generate a signal indicating a presence or an absence of the medical fluid on the surface. The wireless transmitter is configured to transmit the signal to the wireless receiver.

In another aspect, a method includes puncturing, using a needle, an access site on skin of a patient to access a corporeal blood circuit of the patient, and deforming a medical wetness sensing device at a hinge portion of the medical wetness sensing device to place the medical wetness sensing device on a region of the patient surrounding the access site.

Implementations can include one or more of the features described below and herein elsewhere.

In some implementations, the first electrical conductor is interlocked with the second electrical conductor.

In some implementations, the first electrical conductor includes multiple longitudinal segments interconnected by multiple lateral segments.

In some implementations, the second electrical conductor includes a hinge portion enabling a first portion of the second electrical conductor to deflect, at the hinge portion relative to a second portion of the second electrical conductor. The hinge portion of the first electrical conductor and the hinge portion of the second electrical conductor can be collinear.

In some implementations, the first and second electrical conductors include a rigid polymeric material.

In some implementations, the rigid polymeric material has an elastic modulus between 0.1 and 5 GPa.

In some implementations, the hinge portion comprises a living hinge.

In some implementations, the hinge portion of the first electrical conductor has a thickness at most one-half of a maximum thickness of the first electrical conductor.

In some implementations, the first electrical conductor is formed from a polymer loaded with conductive materials.

In some implementations, the medical wetness sensing device includes a first half and a second half. The first half and the second half are defined by a longitudinal axis of the medical wetness sensing device. The first portion of the first electrical conductor can extend through the first half and the second half. The second portion of the first electrical conductor can extend through only the first half.

In some implementations, the hinge portion is a first hinge portion. The first electrical conductor can further include a second hinge portion enabling the second portion of the first electrical conductor to deflect, at the second hinge portion, relative to a third portion of the first electrical conductor.

In some implementations, the first electrical conductor includes bosses. The second electrical conductor can include bosses. The medical wetness sensing device can include a housing coupled to the bosses of the first electrical conductor and the second electrical conductor to separate the first electrical conductor from the second electrical conductor.

In some implementations, the first electrical conductor includes bosses having end portions. The second electrical conductor can include bosses having end portions. The end portions of the bosses of the first electrical conductor and the end portions of the bosses of the second electrical conductor can define a surface of the base to be disposed on the wearer.

In some implementations, the base includes a cover covering at least a portion of the first electrical conductor and at least a portion of the second electrical conductor. In some cases, the medical wetness sensing device further includes a housing within which the controller is contained. The housing can engage the cover to form a fluid tight seal that inhibits entry of fluid into an interior of the housing. In some cases, the cover defines multiple portions of the first electrical conductor that are exposed on a surface of the base to be disposed on the wearer and multiple portions of the second electrical conductor that are exposed on the surface. The controller can be configured to detect the presence of the medical fluid when at least one of the multiple portions of the first electrical conductor and at least one of the multiple portions are electrically connected by the medical fluid. In some cases, the cover includes an elastomeric material.

In some implementations, the medical wetness sensing device further includes a wireless transmitter.

In some implementations, the first portion of the first electrical conductor is positioned at a central portion of the medical wetness sensing device. The second portion of the first electrical conductor can extend radially outward from the central portion. In some cases, the second electrical conductor includes a portion overlying the first portion of the first electrical conductor and positioned at the central portion of the medical wetness sensing device. The medical wetness sensing device can include an insulator positioned between the first portion of the first electrical conductor and the portion of the second electrical conductor to electrically insulate the first electrical conductor from the second electrical conductor. In some cases, the first electrical conductor includes at least three portions extending radially outward from the central portion. In some cases, the first electrical conductor includes at least four portions extending radially outward from the central portion. In some cases, the first electrical conductor includes at least four portions extending radially outward from the central portion. In some cases, the central portion contains the controller. In some cases, the second electrical conductor includes a hinge portion enabling a first portion of the second electrical conductor to deflect, at the hinge portion, relative to a second portion of the second electrical conductor. The hinge portion of the first electrical conductor can be positioned along a first arc of a circle encompassing the central portion, and the hinge portion of the second electrical conductor is positioned along a second arc of the circle.

In some implementations, the dialysis machine is a hemodialysis machine.

In some implementations, the hinge portion includes a living hinge.

In some implementations, the medical wetness sensing device includes a base adapted to be worn on skin of a wearer of the medical wetness sensing device and adapted to contact medical fluid external to the medical wetness sensing device. The base can include a first electrical conductor including a hinge portion. The hinge portion can enable a first portion of the first electrical conductor to deflect, at the hinge portion, relative to a second portion of the first electrical conductor. The base can include a second electrical conductor electrically insulated from the first electrical conductor. The medical wetness sensing device can include a controller electrically connected to the first electrical conductor and the second electrical conductor. The controller can be configured to detect a presence or an absence of the medical fluid electrically connecting the first and second electrical conductors.

In some implementations, the method further includes securing the medical wetness sensing device to the skin with cloth wrapped around an arm of the patient.

In some implementations, the method further includes initiating a hemodialysis treatment using a dialysis machine configured to receive a signal from the medical wetness sensing device. The signal can indicate an absence or presence of a medical fluid on an inner surface of the medical wetness sensing device.

Advantages of the foregoing may include, but are not limited to, one or more of those described below and herein elsewhere.

In some implementations, the flexibility of the wetness sensing device allows the wetness sensing device to conform to underlying geometries of the skin of the patient, the venous needle, and the blood lines, without applying excessive pressure that can cause discomfort for the patient. As a result, the wetness sensing device can contact any blood that leaks from the venous access site, enabling the wetness sensing device to generate signals in response to contact the blood.

The hinge portion of the electrical conductors of the wetness sensing device can reduce the number of components required to enable deflection of the base of the wetness sensing device. In some cases, the hinge portion can be an integral to the electrical conductor such that a separate hinge mechanism or separate deflection mechanism is not necessary to enable deflection of the electrical conductor. The hinge portion can be formed directly into the material forming the electrical conductors. The hinge portion can both enable deflection and enable conduction of electricity.

Because the wetness sensing device can wirelessly communicate a signal indicative of detection of contact between the wetness sensing device and a medical fluid, the wetness sensing device can be a standalone device that is not connected to external systems through wired connections. A patient wearing the wetness sensing device can thus be more easily moved around a treatment environment without disturbing electrical cables and connections between, for example, a dialysis machine and the wetness sensing device.

The details of one or more implementations are set forth in the accompanying drawings and the description below. Other features and advantages will be apparent from the description and drawings, and from the claims.

DESCRIPTION OF DRAWINGS

FIG. 2B is a top view of the wetness sensing device of FIG. 2A.

DETAILED DESCRIPTION

Access to a circulatory system of the patient may require puncturing the skin of a patient using a needle, a catheter, or other devices to form an access. Procedures that can require access to the circulatory system can include dialysis, blood filtration, hemofiltration, blood donation, blood detoxification, apheresis, cardiac catheterizations, among other blood treatment procedures. During a dialysis treatment using a dialysis machine, the needle can place the circulatory system in fluid communication with an extracorporeal system. Blood circulates through the extracorporeal system and undergoes filtering within the extracorporeal system.

In some cases, blood from the patient can leak through the access site onto the skin of the patient. The needle can, for example, dislodge from the access site during treatment due to movement of the patient or inadvertent contact with the needle, which can lead to patient blood loss.

A wetness sensing device placed over the needle and the access site can detect the blood leaking from the access site. Upon detection of a leak, the dialysis machine can alert the patient or an operator of the dialysis machine to resolve the leak, stop the treatment, or otherwise change the course of treatment in response to the leak. The wetness sensing device can be flexible and therefore conformable to the skin of the patient so that the wetness sensing device can be disposed on contours of the patient's body while maintaining close contact with the skin. Blood leakages from the access site can accordingly be quickly and reliably detected.

Overview of System

Figure 1A:
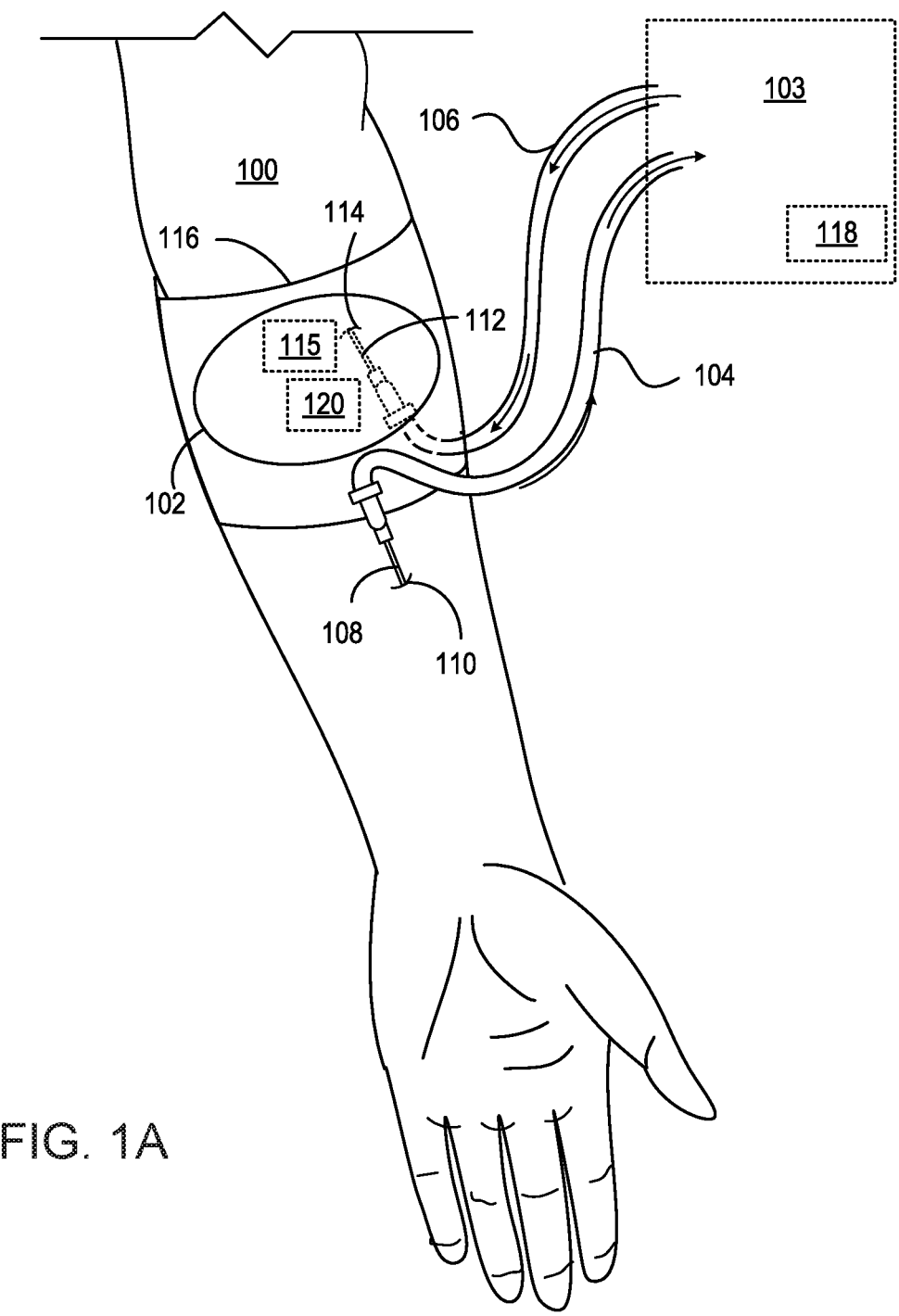
FIG. 1A illustrates an access in an arm of a patient undergoing extracorporeal treatment of blood.

FIG. 1A illustrates a medical wetness sensing device 102 in use on a patient 100 undergoing an extracorporeal treatment (e.g., a dialysis treatment) in which blood from the patient 100 is circulated from the circulatory system of the patient through an extracorporeal system (e.g., a dialysis system) 103. An arterial line 104 moves the blood from the patient 100 to the extracorporeal system 103. The extracorporeal system 103 then returns the blood through a venous line 106 that moves the blood back to the circulatory system of the patient 100.

An arterial needle 108 inserted into an arterial access site 110 of the patient 100 places the circulatory system of the patient 100 in fluid communication with the arterial line 104 and thus the extracorporeal system 103. Similarly, a venous needle 112 inserted into a venous access site 114 places the circulatory system of the patient in fluid communication with the venous line 106 and thus the extracorporeal system 103. The arterial needle 108 and the venous needle 112 are typically inserted into a forearm of the patient 100, but other access sites can be used.

Figure 1B:
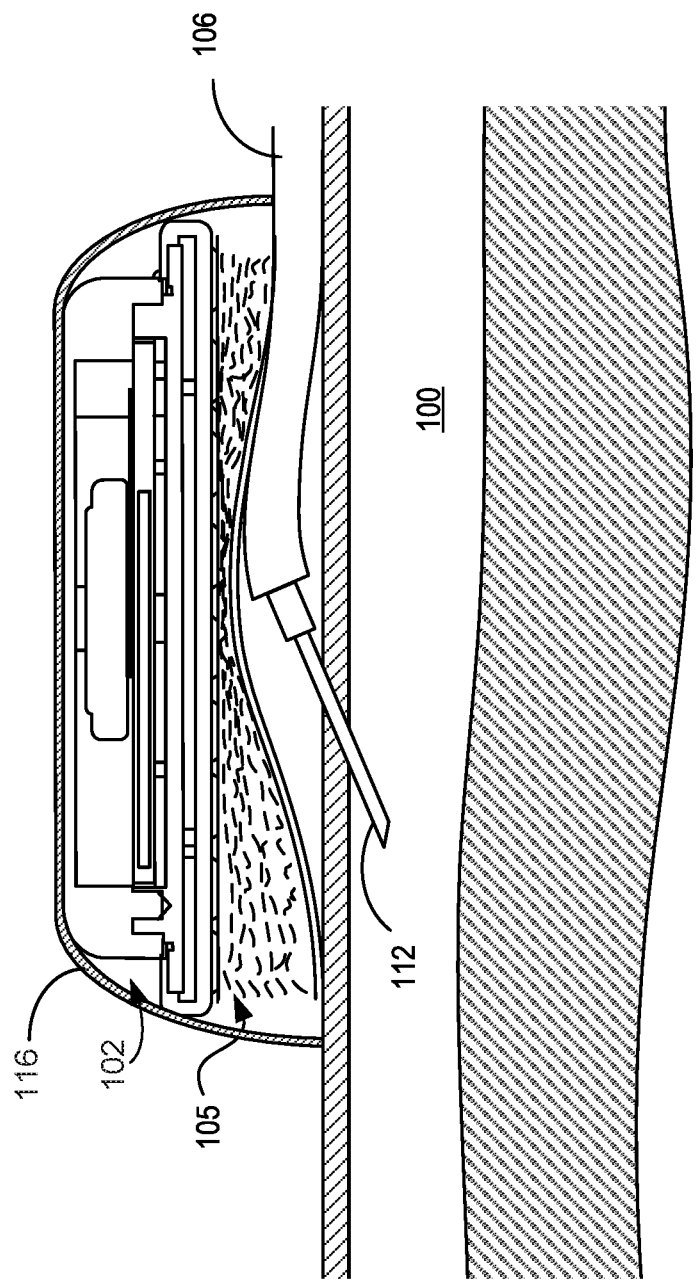
FIG. 1B is a schematic cross-sectional side view of a wetness sensing device used in the extracorporeal treatment of blood shown in FIG. 1A.

As shown in FIG. 1B, the wetness sensing device 102 is flexible, thereby allowing the wetness sensing device 102 to conform to the skin and to the venous needle 112. In particular, an inner surface of the wetness sensing device 102 (e.g., a surface of the wetness sensing device 102 facing the venous access site 114) conforms to the skin. Because of the flexibility of the wetness sensing device 102, the geometry of the inner surface can closely match the geometry of the venous access site.

During use, the wetness sensing device 102 is disposed on the patient with gauze 105 positioned between the wetness sensing device 102 and the skin of the patient 100. The wetness sensing device 102 is positioned over the venous needle 112, and a cloth 116 is wrapped around the wetness sensing device 102 to the fix wetness sensing device 102 in place.

The wetness sensing device 102, in response to detecting leakage of blood, can transmit wireless signals to alert external systems of the leak. The wetness sensing device 102 includes a wireless transceiver 115 (shown in FIG. 1A) that can communicate with a wireless transceiver 118 of the extracorporeal system 103. The wetness sensing device 102 further includes a power source 120 to supply power to the wireless transceiver 115 such that the wetness sensing device 102 does not require a wired power connection to an external power source.

The wetness sensing device 102 can detect absence or presence of a liquid (e.g., blood) on the inner surface of the wetness sensing device 102. Based on the detection, the operator or the extracorporeal system 103 can, for example, change a course of treatment to reduce risk to the patient 100. The wetness sensing device 102 can generate an electrical signal indicating the absence or the presence of blood. The wireless transceiver 115 of the wetness sensing device 102 can receive the electrical signal and generate a wireless signal based on the electrical signal. The wireless transceiver 115 can transmit the wireless signals using a wireless communications technology, such as, Near Field Communication, Bluetooth, or WiFi. The wireless transceiver 118 can receive the wireless signal from the wireless transceiver 115 of the wetness sensing device. Based on the wireless signal, the wireless transceiver 118 can generate electrical signals that the extracorporeal system 103 can use to change the course of treatment.

If the wetness sensing device 102 does not detect blood, the wetness sensing device 102 can generate an electrical signal indicating the absence of blood. The extracorporeal system 103 receives the wireless signal indicating the absence of blood and, in response, can continue with treatment uninterrupted. In some cases, the wetness sensing device 102 can operate in an idle state in which it does not generate the electrical signal in the absence of blood.

In the event that a blood leak occurs due to, for example, dislodgement or disconnection of the venous needle 112, the wetness sensing device 102 can generate a wireless signal indicating the presence of blood. In response to the wireless signal indicating the presence of blood, the extracorporeal system 103 can stop the treatment, reduce a pump speed of a pump of the extracorporeal system 103, or otherwise change the treatment parameters to prevent additional blood leakage. Alternatively or additionally, the extracorporeal system 103 can display an error message or issue an alarm indicating to the operator that the blood leak has occurred. The operator can then resolve the blood leak by changing the treatment parameters or by adjusting components such as, for example, the venous needle 112 and the cloth 116.

Wetness Sensing Devices

A flexible wetness sensing device (e.g., the wetness sensing device 102) that can detect blood leaks from a patient (e.g., the patient 100) can be implemented in a number of ways described herein. FIGS. 2A to 7 depict a first example, and FIGS. 8A to 11 depict a second example. In both of these examples, two electrical conductors are shown. For illustration purposes, exposed surfaces of a first of the electrical conductors are depicted as shaded surfaces and exposed surfaces of a second of the electrical conductors depicted as non-shaded surfaces. The examples set forth herein are merely examples and do not limit the scope of this disclosure.

Referring to FIGS. 2A-2D, a medical wetness sensing device 200 (e.g., the wetness sensing device 102) includes a base 202 and a housing 204. The base 202 is attached to the housing 204 and is adapted to be disposed on the wearer of the medical wetness sensing device 200, e.g., to be secured to the wearer over gauze that has been applied to the skin of the wearer. The base 202 is deflectable, deformable, or both such that it can be placed around contours of the wearer's body. In some examples, the housing 204 does not readily deflect and is relatively more rigid than the base 202.

Figure 2A:
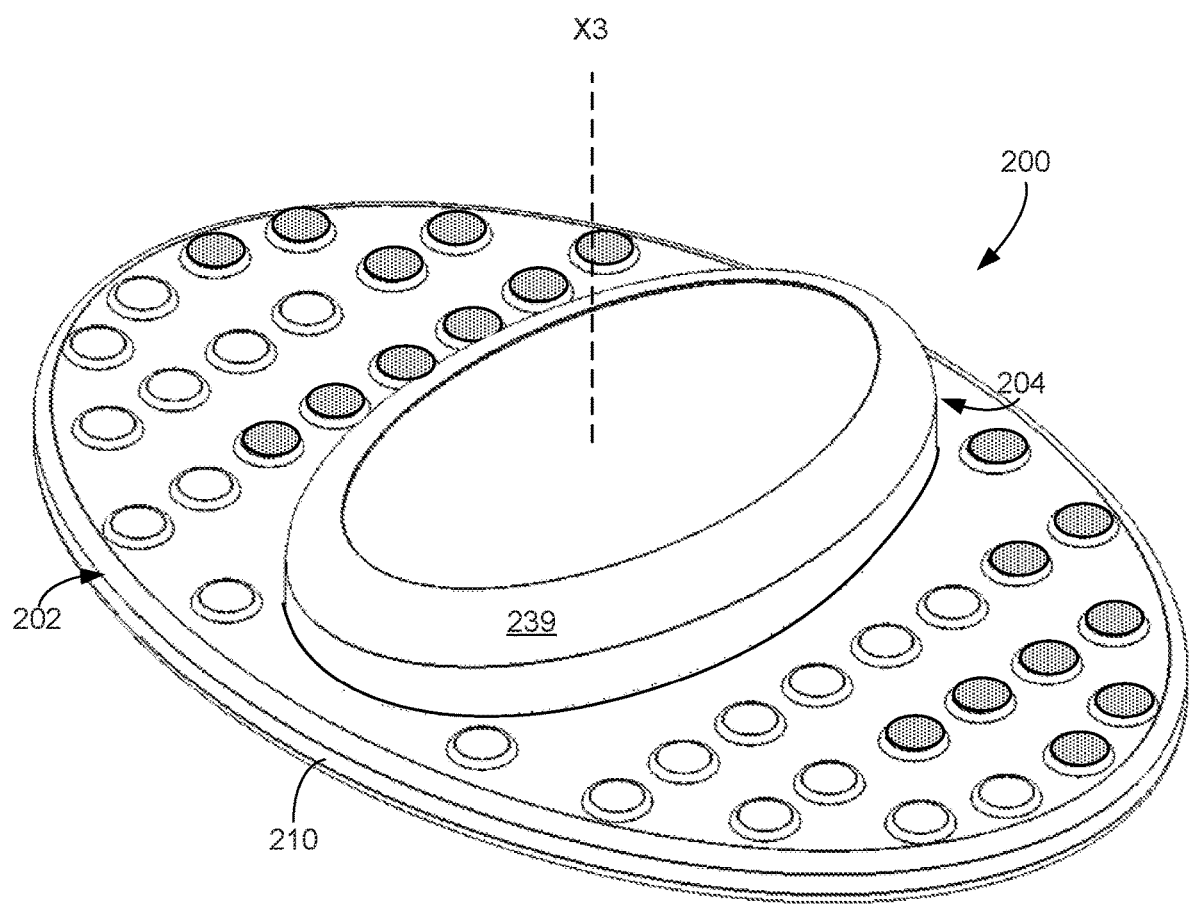
FIG. 2A is a top perspective view of an example of a wetness sensing device.
Figure 2C:
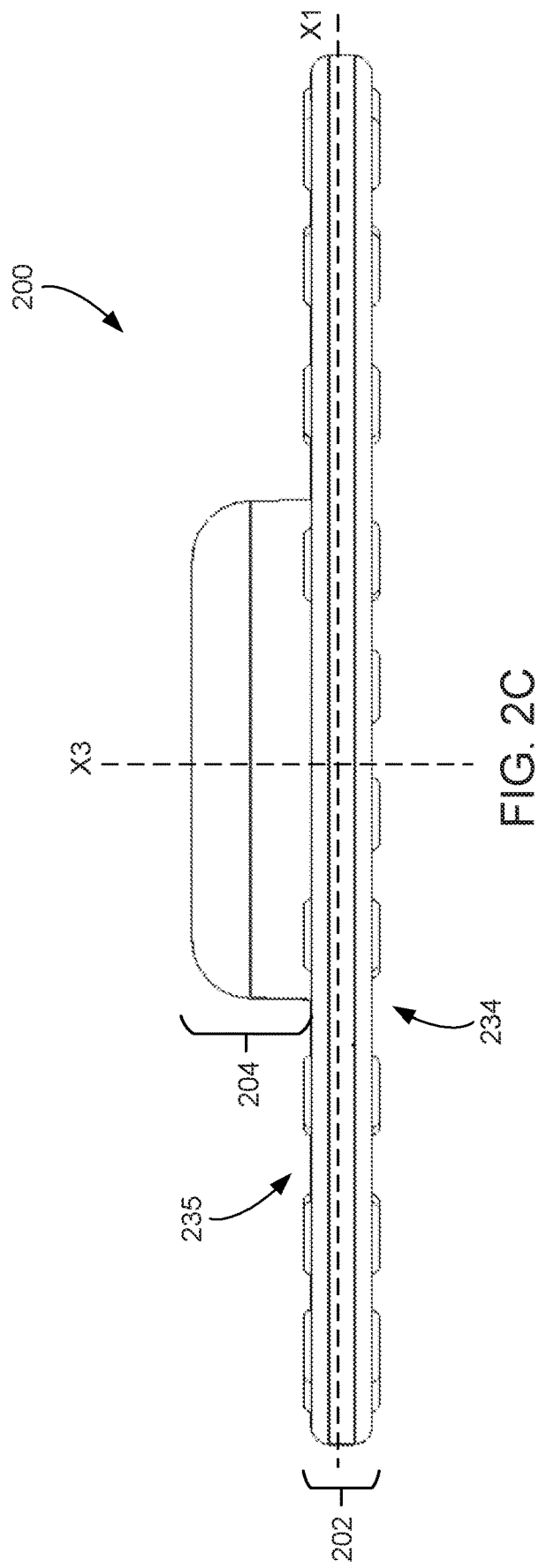
FIG. 2C is side view of the wetness sensing device of FIG. 2A.

Referring to FIG. 2B, the base 202 has an elongate shape that extends outwardly from the housing 204 along a longitudinal axis X1 of the wetness sensing device 200 in two directions. The base 202 has, for example, an oval shape, a rectangular shape, or other elongate shape having a longitudinal axis perpendicular to a longitudinal axis of the housing 204. The longitudinal axis of the base 202 is aligned with the longitudinal axis X1 of the wetness sensing device 200, and the longitudinal axis of the housing 204 is aligned with a transverse axis X2 of the wetness sensing device 200. The housing 204 can have an oval shape, rectangular shape, or other elongate shape. In some examples, the housing 204 has a circular shape and is axisymmetric about a central axis X3 (shown in FIG. 2A). Because the longitudinal axis of the base 202 is transverse to the longitudinal axis of the housing 204, lateral portions 205a, 205b of the base 202 cantilever from the housing 204 a greater distance, thus enabling greater deflection of the base 202. Such a configuration of the housing 204 and the base 202 can enable greater unidirectional or bidirectional bending of the base 202 about the longitudinal axis X2 of the housing 204. For example, the base 202 can bend upward toward the housing 204 and/or downward away from the housing 204.

Figure 3:
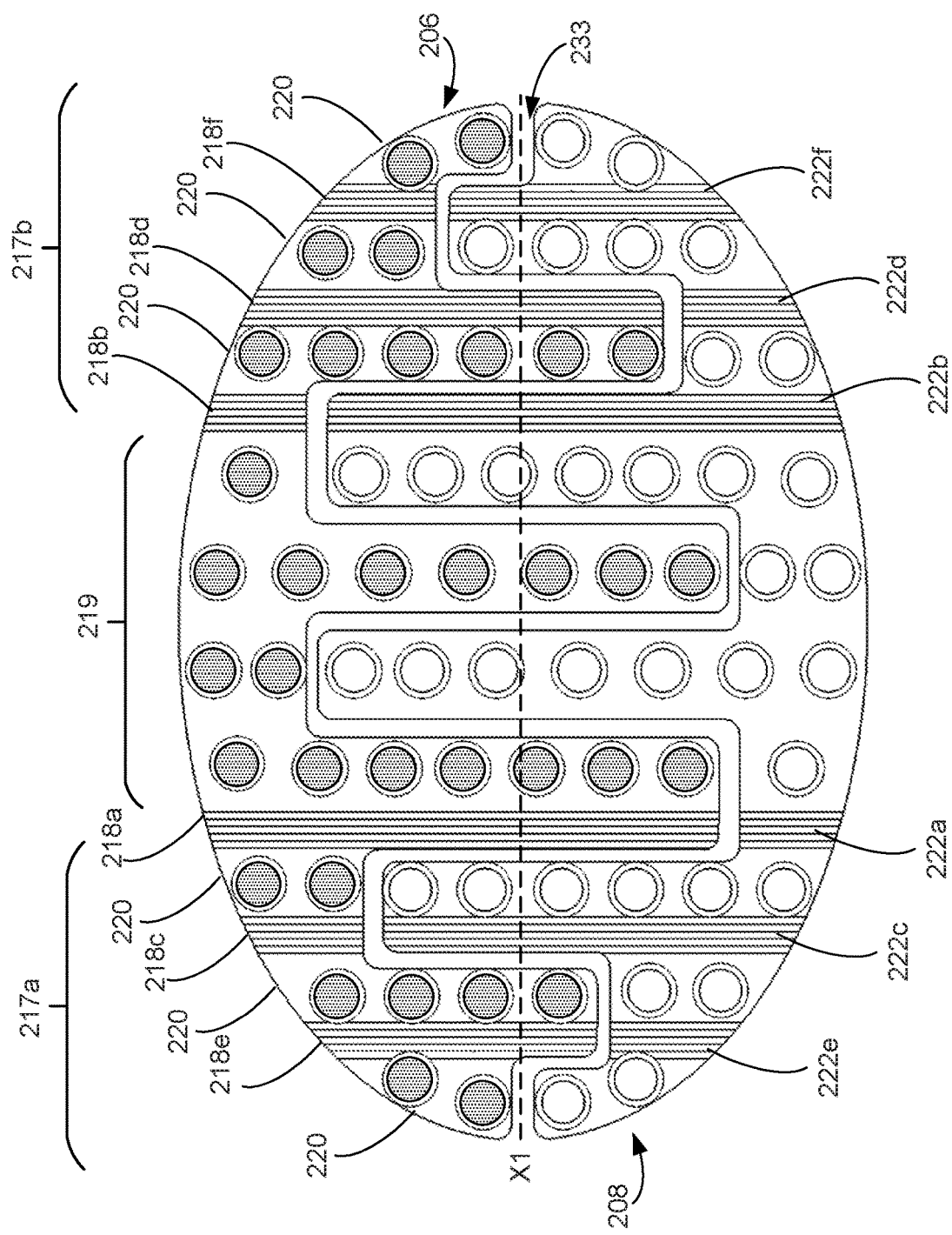
FIG. 3 is a bottom view of electrical conductors of the wetness sensing device of FIG. 2A.

The base 202 includes a first electrical conductor 206, a second electrical conductor 208, and a cover 210. FIG. 3 shows a bottom view of the first and second electrical conductors 206, 208 isolated from other components of the wetness sensing device 200. The first and the second electrical conductors 206, 208 are electrically conductive but are electrically isolated from one another. For example, the first and second electrical conductors 206, 208 can be insulated from one another. As described herein, the first and second electrical conductors 206, 208 are formed of a rigid material and are deflectable about hinge portions.

In some examples, the first and second electrical conductors 206, 208 are formed of a polymer loaded with conductive materials. The conductive materials increase electrical conductivity of the polymer so that electrical signals can be transmitted through the electrical conductors 206, 208. In some examples, the first and second electrical conductors 206, 208 are composited with black carbon, graphene flakes, carbon nanotubes, silver, nickel, silver-coated fibers, metal fibers, metal mesh, or other conductive materials that allow the first and electrical conductors 206, 208 to be conductive.

Both the first and second electrical conductors 206, 208 extend along a length L1 (shown in FIG. 2B) of the wetness sensing device 200, e.g., along an entirety of the length L1. The first and second electrical conductors 206, 208 extend along a portion of a width W1 of the wetness sensing device 200. The conductors 206, 208 can have a maximum width between 50% and 90% of the width W1 of the wetness sensing device 200, e.g., between 50% and 70%, 60% and 80%, 70% and 90%, etc., of the width W1.

Figure 4A:
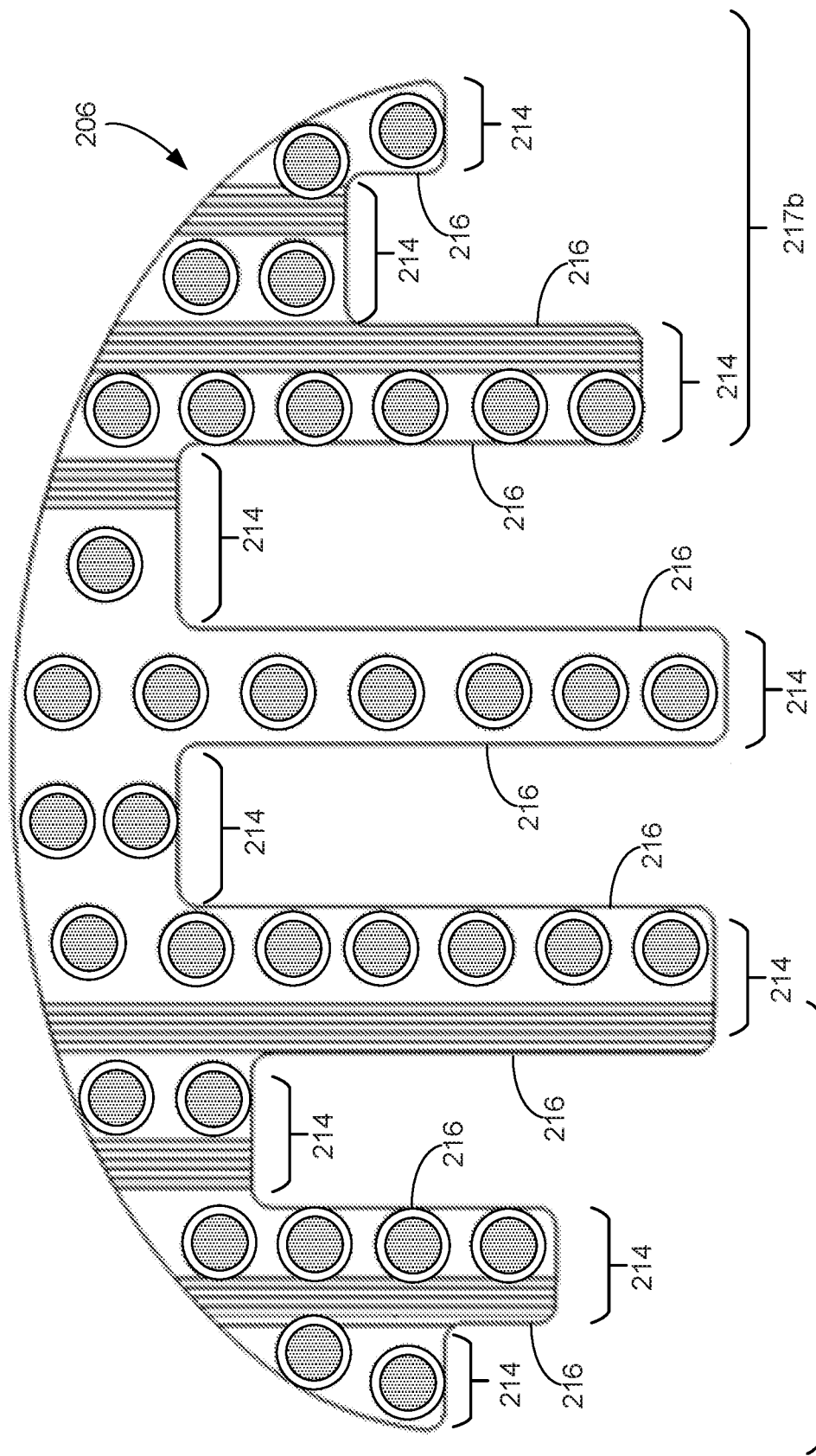
FIG. 4A is a bottom view of an electrical conductor of the wetness sensing device of FIG. 2A.

Referring to FIG. 4A depicting a bottom view of the first electrical conductor 206, the first electrical conductor 206 has a perimeter defined by an outer perimeter 212 of the wetness sensing device 200 (shown in FIG. 2B) and a series of alternating longitudinal segments 214 and transverse segments 216. In particular, the longitudinal segments 214 are interconnected by the transverse segments 216. The longitudinal segments 214 extend along axes parallel to the longitudinal axis X1 of the wetness sensing device 200, and the transverse segments 216 extend along axes transverse to the longitudinal axis X1 of the wetness sensing device 200. While ten longitudinal segments 214 and nine transverse segments 216 are shown in FIG. 3, in some implementations, the first electrical conductor 206 includes fewer or more longitudinal segments, e.g., 9 or less, 11 or more, etc., and/or fewer or more transverse segments, e.g., 8 or less, 10 or more, etc.

Figure 4B:
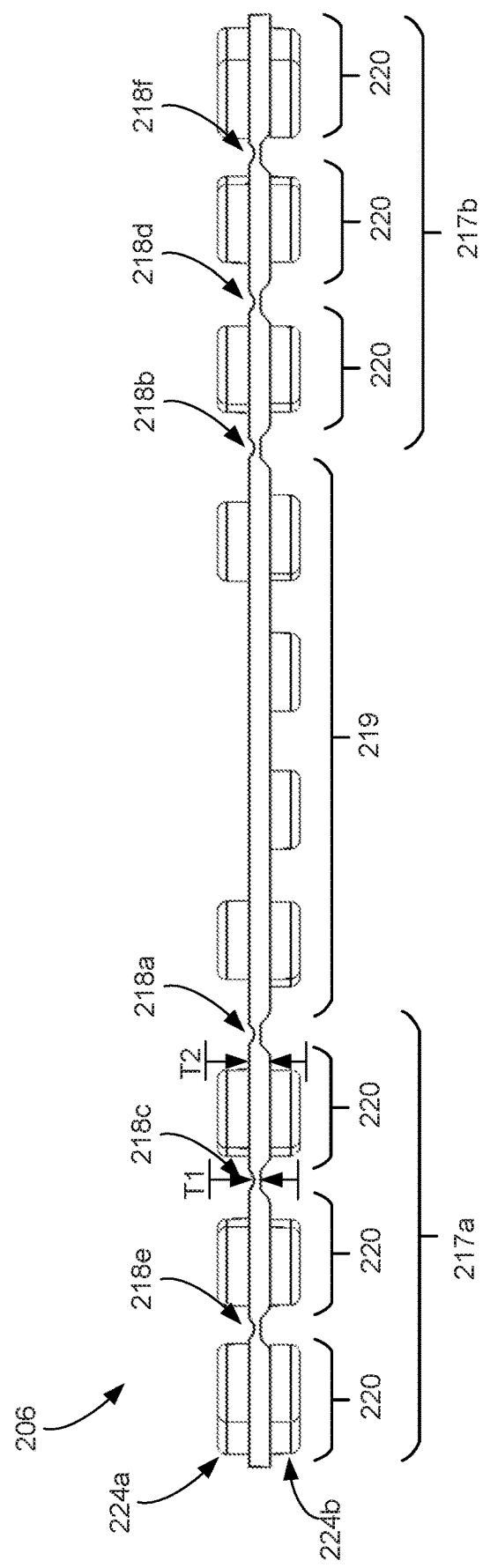
FIG. 4B is a side view of the electrical conductor of FIG. 4A.

Referring to FIG. 4B depicting a side view of the first electrical conductor 206, the lateral portions 217a, 217b of the first electrical conductor 206 include hinge portions 218a-218f (collectively referred to as hinge portions 218). The hinge portions 218 are electrically conductive portions of the electrical conductors 206, 208. In addition, the hinge portions 218 enable deflection of the lateral portions 217a, 217b relative to a central portion 219 of the first electrical conductor 206 as well as deflection within the lateral portions 217a, 217b. The lateral portions 217a, 217b are part of the lateral portions 205a, 205b (described with respect to FIG. 2B) of the wetness sensing device 200, and the central portion 219 of the first electrical conductor 206 is positioned within a region beneath the housing 204 of the wetness sensing device 200. The hinge portions 218a-218f each extend transversely along the first electrical conductor 206, e.g., across an entire width of the first electrical conductor 206, to enable deflection about the transverse axis X2 of the wetness sensing device 200.

Hinge portions 218a, 218b connect the lateral portions 217a, 217b, respectively to the central portion 219. The lateral portion 217a is deflectable, at the hinge portion 218a, relative to the central portion 219 of the first electrical conductor 206. The lateral portion 217b is deflectable, at the hinge portion 218b, relative to the central portion 219 of the first electrical conductor 206. For example, the lateral portions 217a, 217b are deflectable, in their entireties, about the hinge portions 218a, 218b. The lateral portions 217a, 217b are deflectable about the transverse axis X2 of the wetness sensing device 200, e.g., away from the housing 204 or toward the housing 204.

Hinge portions 218c-218f enable relative deflection of sections 220 of the lateral portions 217a, 217b. The sections 220 are connected to one another by the hinge portions 218c-218f, and adjacent sections 220 are deflectable relative to one another at the hinge portions 218c-218f. The sections 220 are deflectable at the hinge portions 218a-218f about the transverse axis X2 of the wetness sensing device 200, e.g., away from the housing 204 or toward the housing 204.

In the illustrated example, the hinge portions 218 include living hinges. The living hinges correspond to portions of the first electrical conductor 206 thinner than other portions of the first electrical conductor 206 surrounding the living hinges. The first electrical conductor 206 can be formed from a rigid material such that the thinner portions corresponding to the living hinges have reduced stiffness and thus enable deflection of the first electrical conductor 206. The first electrical conductor 206 is monolithic such that the central portion 219 and the lateral portions 217a, 217b are formed from the same material. In this regard, the hinge portions 218 are formed from this same material. The material can be, for example, a rigid polymeric material, such as polycarbonate, polypropylene, polyethylene, etc. The elastic modulus of the material can be, for example, between 0.1 and 5 GPa, e.g., between 0.1 and 0.5 GPa, 0.5 and 3 GPa, 1 GPa, and 3.5 GPa, 2 GPa and 5 GPa, etc.

To enable deflection at the hinge portions 218, the hinge portions 218 have a stiffness less than a stiffness of portions surroundings the hinge portions 218, e.g., less than the sections 220 and the central portion 219. The hinge portions 218, for example, have a thickness T1 that is less than a thickness T2 of the rest of the first electrical conductor 206, e.g., the sections 220 and the central portion 219. The hinge portions 218 are flexible portions of the first electrical conductor that enable deflection, and the sections 220 and the central portion 219 are rigid portions that deflect, e.g., in their entireties, relative to the hinge portions 218. The thickness T1 is, for example, 5% to 50% of the thickness T2, e.g., between 5% and 20%, 15% and 30%, 25% and 40%, 35% and 50%, at most 50%, at most 40%, at most 30%, etc., of the thickness of T2. The relatively lower thickness T1 of the hinge portions 218 reduces the stiffness of the hinge portions 218. In some implementations, the thickness T1 is between, for example, 0.1 mm to 1 mm, e.g., between 0.1 mm and 0.7 mm, 0.2 mm and 0.8 mm, 0.3 mm and 0.9 mm, 0.4 mm and 1 mm, etc. In some implementations, the thickness T2 corresponds to a maximum thickness of the first electrical conductor 206.

As shown in FIG. 2B, the longitudinal axis X1 defines a first half 221a of the wetness sensing device 200 and a second half 221b of the wetness sensing device 200. The first electrical conductor 206 is positioned on the first half 221a with each of the sections 220, the hinge portions 218, and the central portion 219 extending through the first half 221a. At least some of the portions of the first electrical conductor 206 extend through the second half 221b. As shown in FIG. 4A, the central portion 219 includes sections extending through both the first half 221a and the second half 221b. The central portion 219 further includes sections extending through only the first half 221a. In each of the lateral portions 217a, 217b, one or more of the sections 220 of the lateral portions 217a, 217b extend through both the first half 221a and the second half 221b, and one or more of the sections 220 extend through only the first half 221a.

Referring back to FIG. 3, the first electrical conductor 206 is interlocked with the second electrical conductor 208. The first and second electrical conductors 206, 208 overlap one another along the longitudinal axis X1 of the wetness sensing device 200. While specific configurations of the first electrical conductor 206 are described with respect to FIGS. 4A and 4B, example configurations of the second electrical conductor 208 are similar. For example, the second electrical conductor 208 can include transverse segments and longitudinal segments to match the transverse segments 216 and the longitudinal segments 214 of the first electrical conductor 206.

The second electrical conductor 208 includes hinge portions 222a-222f and is deflectable in a manner similar to the first electrical conductor 206. In this regard, the hinge portions 222a-222f extend parallel to the transverse axis X2. The hinge portions 222a-222f can be, for example, collinear with the hinge portions 218a-218f, respectively. The hinge portions 222a-222f and the hinge portions 218a-218f are all parallel to one another. The first and second electrical conductor 206, 208 are therefore both deflectable about the transverse axis X2, enabling the wetness sensing device 200 to be easily wrapped around contours when worn on the patient's body.

Rather than being positioned on the first half 221a, the second electrical conductor 208 is positioned on the second half 221b, with each of its sections, hinge portions, and central portion extending through the second half 221b. In addition, at least some of the portions of the second electrical conductor 208 extend through the first half 221a. As described herein, because at least some portions of both of the first and second electrical conductors 206, 208 extend through both halves 221a, 221b of the wetness sensing device 200, the first and second electrical conductors 206, 208 are both more easily exposed to medical fluid present along an inner surface 234 of the base 202 (shown in FIG. 2C) and thus can more easily detect the medical fluid. The inner surface 234 includes a surface applied to or over skin of the wearer of the wetness sensing device 200.

Figure 2D:
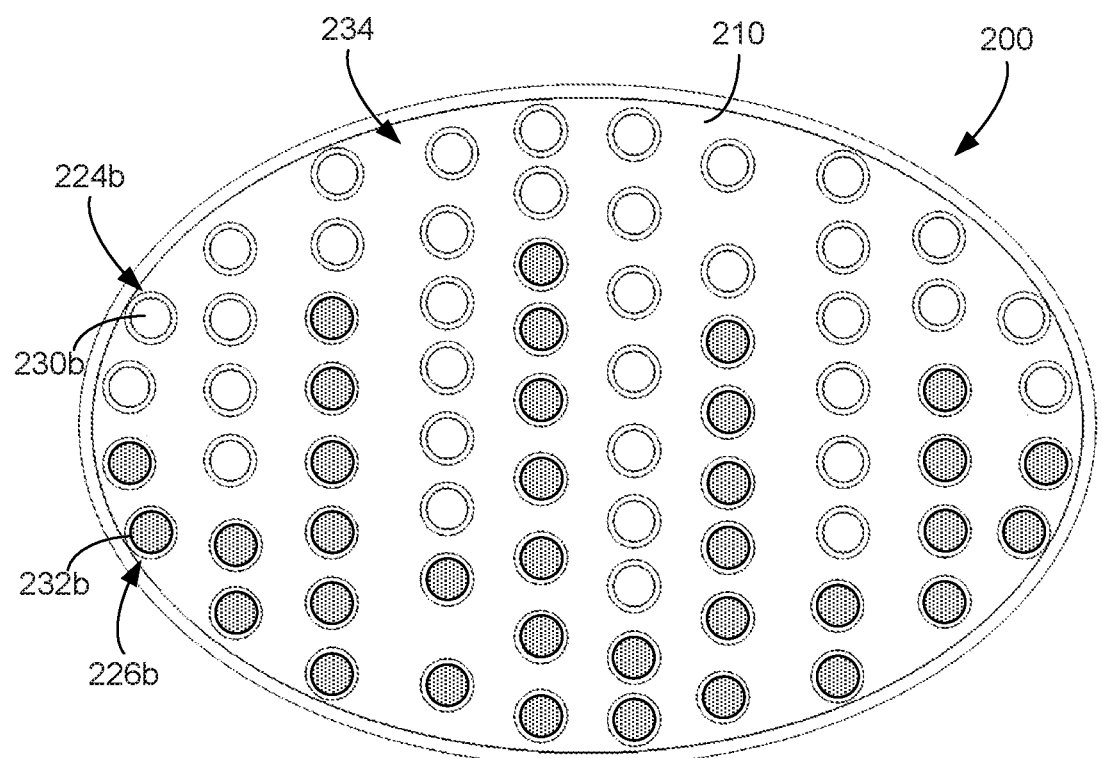
FIG. 2D is a bottom view of the wetness sensing device of FIG. 2A.

Referring to FIGS. 2B and 2D, the first electrical conductor 206 includes bosses 224a, 224b extending in directions parallel to a central axis X3 (shown in FIG. 2A). The second electrical conductor 208 also includes bosses 226a, 226b extending in directions parallel to the central axis X3. The bosses 224a and 226a extend along axes parallel to the central axis X3 toward the housing 204 of the wetness sensing device 200 and away from the skin of the patient when the wetness sensing device 200 is disposed on the patient. The bosses 224b, 226b extend along axes parallel to the central axis X3 away from the housing 204 of the wetness sensing device 200 and toward the skin of the patient when the wetness sensing device 200 is disposed on the patient.

Figure 5:
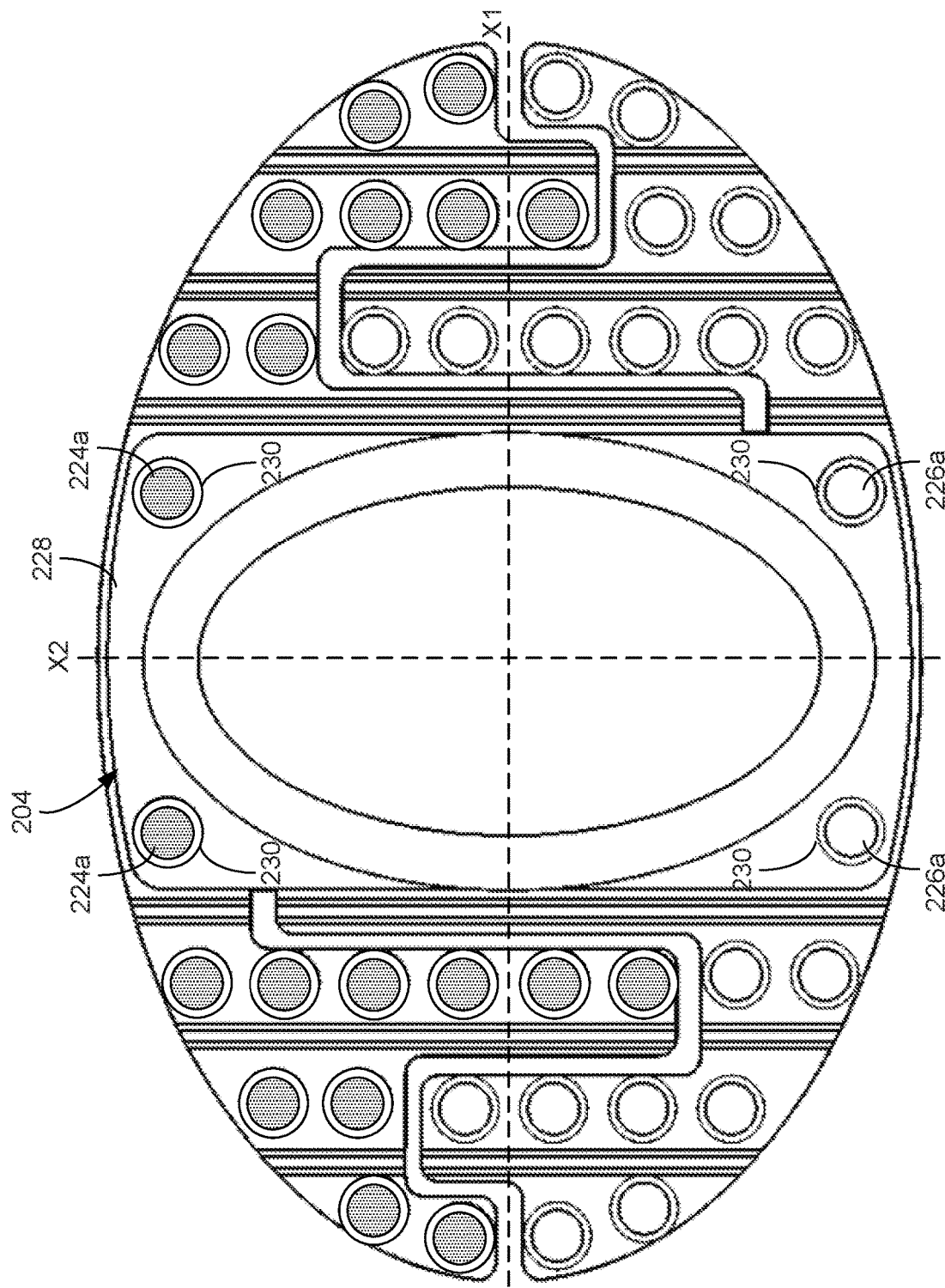
FIG. 5 is a top view of the wetness sensing device of FIG. 2A with a cover of the wetness sensing device removed.

Referring to FIG. 5, which shows the electrical conductors 206, 208 and the housing 204 isolated from the cover 210, the bosses 224a, 226a are directly engaged with a lower housing portion 228 of the housing 204. The lower housing portion 228 includes openings 230 to engage with the bosses 224a of the first electrical conductor 206 and the bosses 226a of the second electrical conductor 206. For example, the bosses 224a, 226a extend through the openings 230 to engage the lower housing portion 228. Engagement between the bosses 224a, 226a and the lower housing portion 228 inhibits relative translation of the electrical conductors 206, 208 and the housing 204, e.g., along the transverse axis X2 and along the longitudinal axis X1. In addition, because the lower housing portion 228 is engaged with at least two bosses 224a of the first electrical conductor 206 and with at least two bosses 226a of the second electrical conductor 208, rotation of the first and second electrical conductors 206, 208 about the central axis X3 is inhibited.

When engaged to the bosses 224a, 226a, the lower housing portion 228 locks positions of the first electrical conductor 206 and the second electrical conductor 208 such that the conductors 206, 208 are separated from one another. For example, the conductors 206, 208 are locked in positions in which they do not directly contact one another. The cover 210 is positioned between the first electrical conductor 206 and the second electrical conductor 208, thereby separating and electrically insulating the first electrical conductor 206 from the second electrical conductor 208.

Referring to FIG. 3, a separation 233 between the first electrical conductor 206 and the second electrical conductor 208 is defined by, for example, the engagement between the lower housing portion 228 and the bosses 224a, 226a. The separation 233 extends along the longitudinal segments and the transverse segments of the electrical conductors 206, 208. The separation 233 can have a width between, for example, 0.5 millimeters and 4 millimeters, e.g., between 0.5 millimeters and 1 millimeter, 1 millimeter and 2 millimeters, or 2 millimeters and 4 millimeters, etc. The separation 233 ensures electrical discontinuity between the first electrical conductor 206 and the second electrical conductor 208 such that electrical continuity between the electrical conductors 206, 208 can serve as an indicator of a presence of a conductive medium, e.g., a medical fluid, electrically connecting the first and second electrical conductors 206, 208.

Referring back to FIG. 2D, the bosses 224b, 226b have end portions 230b, 232b defining the inner surface 234 of the base 202. As described herein, the inner surface 234 is adapted to be disposed on the wearer of the wetness sensing device 200. In some implementations, referring to FIG. 2B, the bosses 224a, 226a also have end portions 230a, 232a defining an outer surface 235 of the base 202. The inner surface 234 is a surface of the wetness sensing device 200 that faces skin of a wearer of the wetness sensing device 200 and that is placed and pressed against the wearer or against gauze applied to the wearer. The inner surface 234 of the wetness sensing device 200 contacts the wearer, the gauze, or both. When the inner surface 234 is placed against the wearer, the base 202 of the wetness sensing device 200 deflects to conform to the skin and the venous needle, thus enabling the inner surface 234 to be easily in contact with medical fluid leaking from the venous needle.

The other portions of the inner surface 234 of the base 202 are defined by the cover 210. The cover 210 can be formed from a material that is more flexible than the material forming the first and second electrical conductors 206, 208. The cover 210 can be formed from, for example, a flexible elastomeric material such as rubber, silicone, ethylene propylene diene monomer (EPDM) rubber, fluorocarbon rubber, silicone rubber, fluorosilicone rubber, polyether block amides, Chloropene rubber, Butyl rubber, among other elastomeric materials, etc. The cover 210 can have a low modulus of elasticity of, for example, 0.1 MPa to 100 MPa, e.g., 0.01 MPa to 1 MPa, 1 MPa to 10 MPa, or 10 MPa to 20 MPa, etc. The cover 210 can withstand large strains of between at least, for example, 10% and 20% (e.g., between at least 10% to 15%, 15% to 20%) without resulting in damage to the cover 210.

The cover 210 extends across both top and bottom portions of the electrical conductors 206, 208. The first and second electrical conductors 206, 208 are exposed along the inner surface 234 of the wetness sensing device 200. For example, the end portions 230b, 232b of the bosses 224b, 226b extend through the cover 210 such that the end portions 230b, 232b are exposed on the inner surface 234 of the base 202. The end portions 230b, 232b are exposed in this way to medical fluid that may contact the inner surface 234 during a treatment. In some implementations, the end portions 230a, 232a extend through the cover 210 such that the end portions 230a, 232a are exposed to medical fluid that may contact the outer surface 235 during a treatment. Blood that leaks from the wearer contacts the inner surface 234 and thus contacts the first and second electrical conductors 206, 208 and the cover 210. In some cases, the leaked blood is absorbed by the gauze and in turn contacts the inner surface 234. Because at least some of the sections of the first electrical conductor 206 extend through the second half 221b and at least some of the sections of the second electrical conductor 208 extend through the first half 221a, the blood present on the inner surface 234 can be more likely to contact both the first and second electrical conductor 206, 208. In this regard, the presence of the blood can be more easily detected.

The housing 204 contains electronic components to facilitate detection of medical fluid contact with the electrical conductors 206, 208 of the wetness sensing device 200. Referring back to FIG. 2A, an upper housing portion 239 of the housing 204 engages the cover 210 to form a fluid tight seal that inhibits entry of fluid into an interior of the housing 204. The upper housing portion 239 compresses the cover 210 to form the fluid tight seal.

In some examples, to manufacture the wetness sensing device 200, the lower housing portion 228 is engaged to the first and second electrical conductors 206, 208, as shown in FIG. 5. The cover 210 is then molded to the conductors 206, 208 and to the lower housing portion 228 in an overmolding operation. The electrical components are then placed in the lower housing portion 228. The upper housing portion 239 is then positioned on the lower housing portion 228 and locked to the lower housing portion 228. The upper housing portion 239 is pushed against the cover 210 when it is positioned on the lower housing portion 228 to form the fluid tight seal separating the interior of the housing 204 from an external environment. This can prevent medical fluid from infiltrating into the interior of the housing 204 and damaging electrical components contained within the housing 204.

Figure 6:
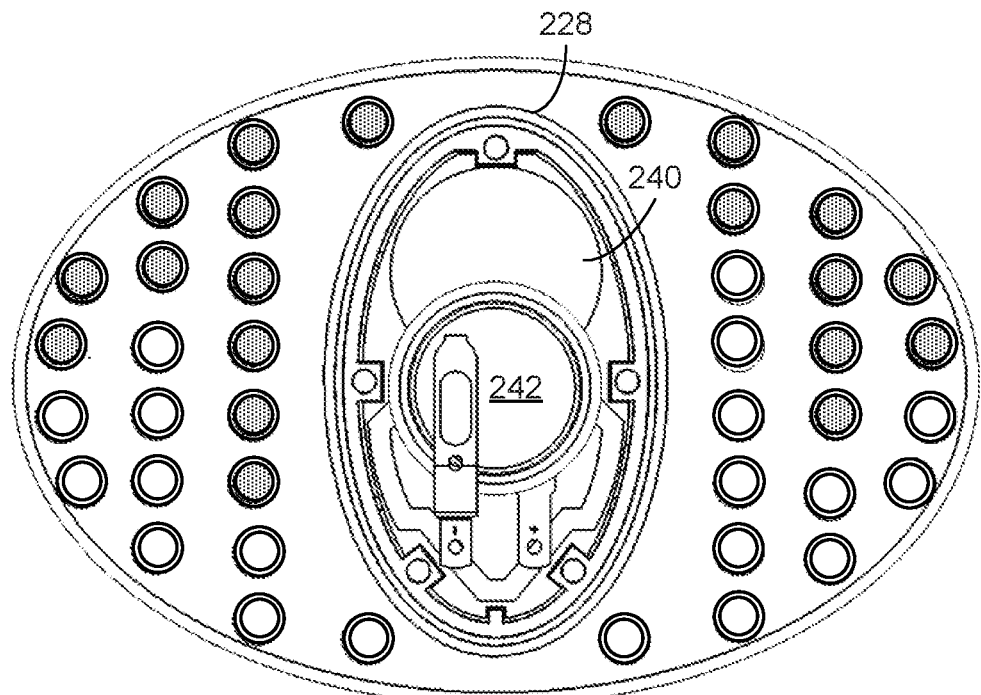
FIG. 6 is a top view of the wetness sensing device of FIG. 2A with an upper housing portion removed.
Figure 7:
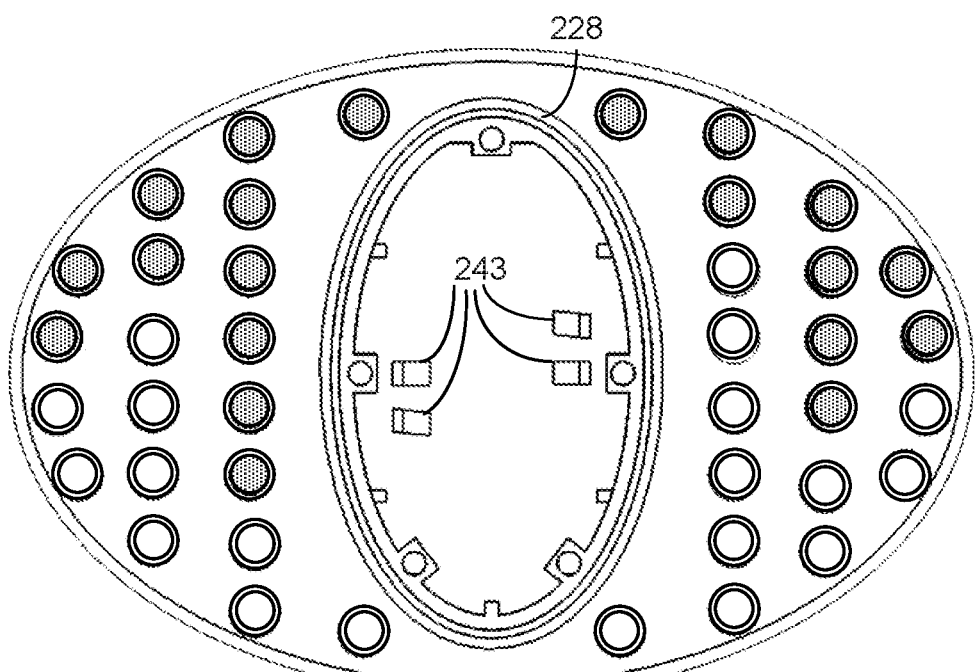
FIG. 7 is a top view of the wetness sensing device of FIG. 2A with the upper housing portion, circuitry, and a power source removed.

As shown in FIG. 6, control circuitry 240 is contained within the housing 204. The control circuitry 240 can include appropriate electrical components to control operations of the control circuitry 240 described herein. The control circuitry 240 can include a microcontroller to process, generate, transmit, and receive electrical signals. The control circuitry 240 is electrically connected to the first electrical conductor 206 and the second electrical conductor 208. Referring to FIG. 7, the lower housing portion 228 includes openings 243 to provide access for wired electrical connections between the first electrical conductor 206 and the control circuitry 240 and wired electrical connections between the second electrical conductor 208 and the control circuitry 240.

The control circuitry 240 can detect electrical continuity between the first and second electrical conductors 206, 208 by transmitting electrical test signals through the first and second electrical conductors 206, 208. For example, the control circuitry 240 can transmit the test signals through one of the first and second electrical conductors 206, 208 and determine whether the test signals propagate through the other electrical conductor.

The control circuit 240 is configured to detect a presence or an absence of a medical fluid electrically connecting the first and second electrical conductors 206, 208. In the absence of medical fluid, such as blood, the control circuitry 240 can detect that the first and second electrical conductors 206, 208 do not form a closed electrical loop. In the presence of medical fluid, the control circuitry 240 can detect that the first and second electrical conductors 206, 208 form a closed electrical loop (e.g., are electrically continuous). In particular, the medical fluid can contact both the end portions 230a, 230b of the first electrical conductor 206 and the end portions 232a, 232b of the second electrical conductor to form the closed electrical loop. In the presence of the medical fluid, the electrical test signal transmitted through the first and second electrical conductors 206, 208 indicate electrical continuity between the first electrical conductor 206 and the second electrical conductor 208.

The control circuitry 240 can determine that an electrical resistance below a predetermined threshold indicates that the first and second electrical conductors 206, 208 form the closed electrical loop or are electrically continuous. Electrical resistances below a threshold between, for example, 500 Kohms and 1 Mohm can indicate electrical continuity between the first and second electrical conductors that could occur in the presence of medical fluid.

In response to detecting electrical continuity through the first and second electrical conductors 206, 208, the control circuitry 240 can generate an electrical signal indicating the presence of medical fluid along the inner surface 234 of the base 202. Similarly, in response to detecting electrical isolation between the first and second electrical conductors 206, 208 (e.g., the first and second electrical conductors 206, 208 are not electrically connected), the control circuitry 240 can generate an electrical signal indicating the absence of medical fluid along the inner surface 234. In some cases, in response to detecting the electrical isolation, the control circuitry 240 can simply not transmit an electrical signal. The first and second electrical conductors 206, 208 are thus configured to cause the control circuitry 240 to generate a signal indicating the absence or presence of medical fluid on the inner surface 234.

The control circuitry 240 can include a wireless transceiver, which can, based on the electrical signal, generate a wireless signal indicating the absence of medical fluid or the presence of medical fluid. The wireless signal can be transmitted to a wireless transceiver of an extracorporeal system, a dialysis machine, or other treatment device (e.g., the wireless transceiver 115 of FIG. 1A). The wireless transceiver can transmit the wireless signal until the wireless transceiver receives a wireless stop signal including instructions to stop transmitting the wireless signal. For example, the treatment device can transmit a wireless stop signal to the wireless transceiver after the medical fluid leak causing the presence of the medical fluid has been resolved.

The control circuitry 240 receives power from a power source 242 to execute various electrical operations. The control circuitry 240 can use the power to transmit the test signals to detect an absence or presence of electrical continuity that can be caused by the absence or presence of medical fluid on the inner surface 234 of the base 202. In some implementations, the power source 242 is removably housed in the housing 204. The upper housing portion 239 is removable from the lower housing portion 228 so that the power source 242 can be removed and inserted. As a result, the power source 242 can be replaceable in an event that the power source 242 does not have sufficient power to energize the control circuitry 240.

While in the absence of medical fluid, the wetness sensing device 200 can operate in an idle state in which the control circuitry 240 transmits the electrical test signals without generating the electrical signal and the wireless signal. The idle state has a reduced power requirement, as the control circuitry 240 does not operate the wireless transceiver during the idle state.

Figure 8A:
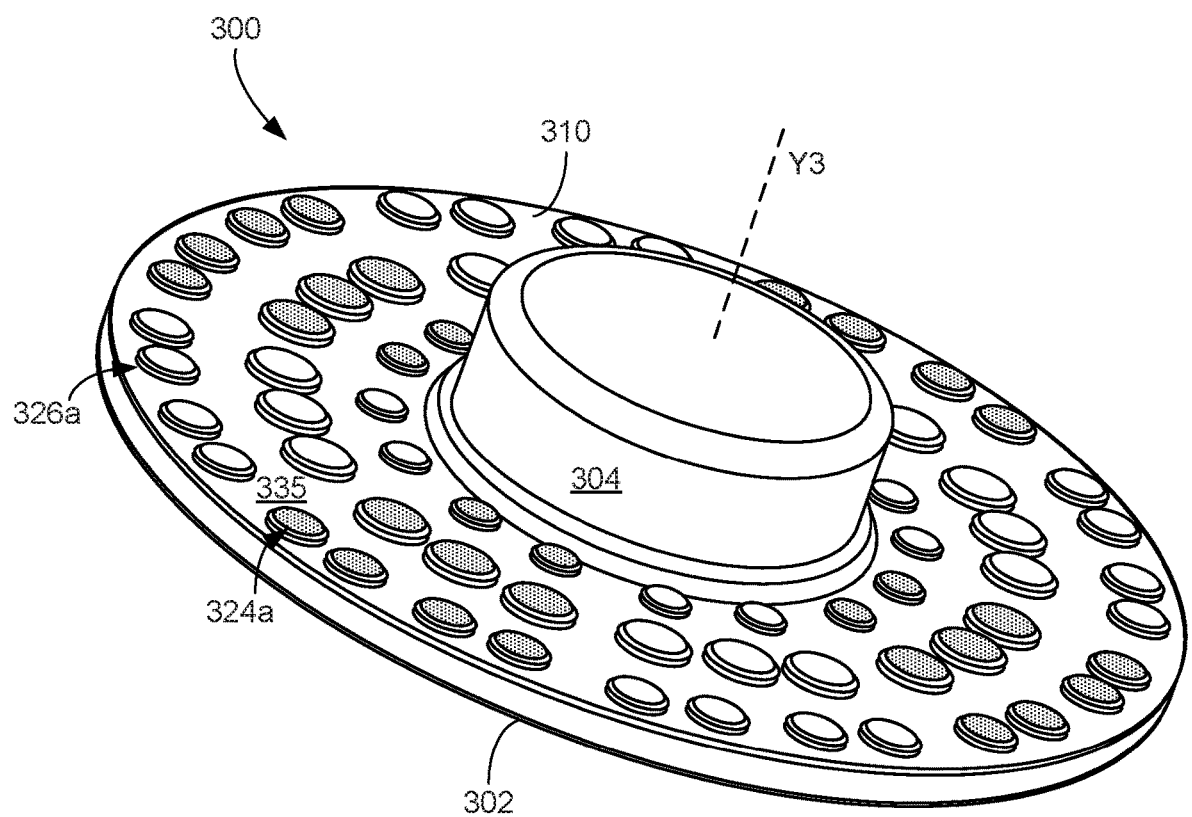
FIG. 8A is a top perspective view of another example of a wetness sensing device.

FIGS. 8A-12 describe a wetness sensing device 300 in accordance with additional implementations. Referring to FIGS. 8A-8C, the wetness sensing device 300 differs from the wetness sensing device 200 in that the wetness sensing device 300 has a base 302 that extends radially outward from a housing 304 of the wetness sensing device 300. The base 302 extends in directions along both a longitudinal axis Y1 and a transverse axis Y2 of the wetness sensing device 300. Because the base 302 extends in both directions, the base 302 is deflectable about both the longitudinal axis Y1 and the transverse axis Y2, thus providing greater degrees of freedom of bending what is provided by the base 202 of the wetness sensing device 200. Whereas the longitudinal axis X1 of the wetness sensing device 200 is typically aligned with curvature of the patient's body so that the base 202 can be wrapped around the patient's body, the base 302 can be placed on the patient's body in any orientation of the longitudinal axis Y1 and the transverse axis Y2. The base 302 can have, for example, a shape that is axisymmetric about a central axis Y3 of the wetness sensing device 300. The base 302 can be, for example, circular, with a center of the circle defining the base 302 coinciding with the central axis Y3 of the wetness sensing device 300.

Figure 9:
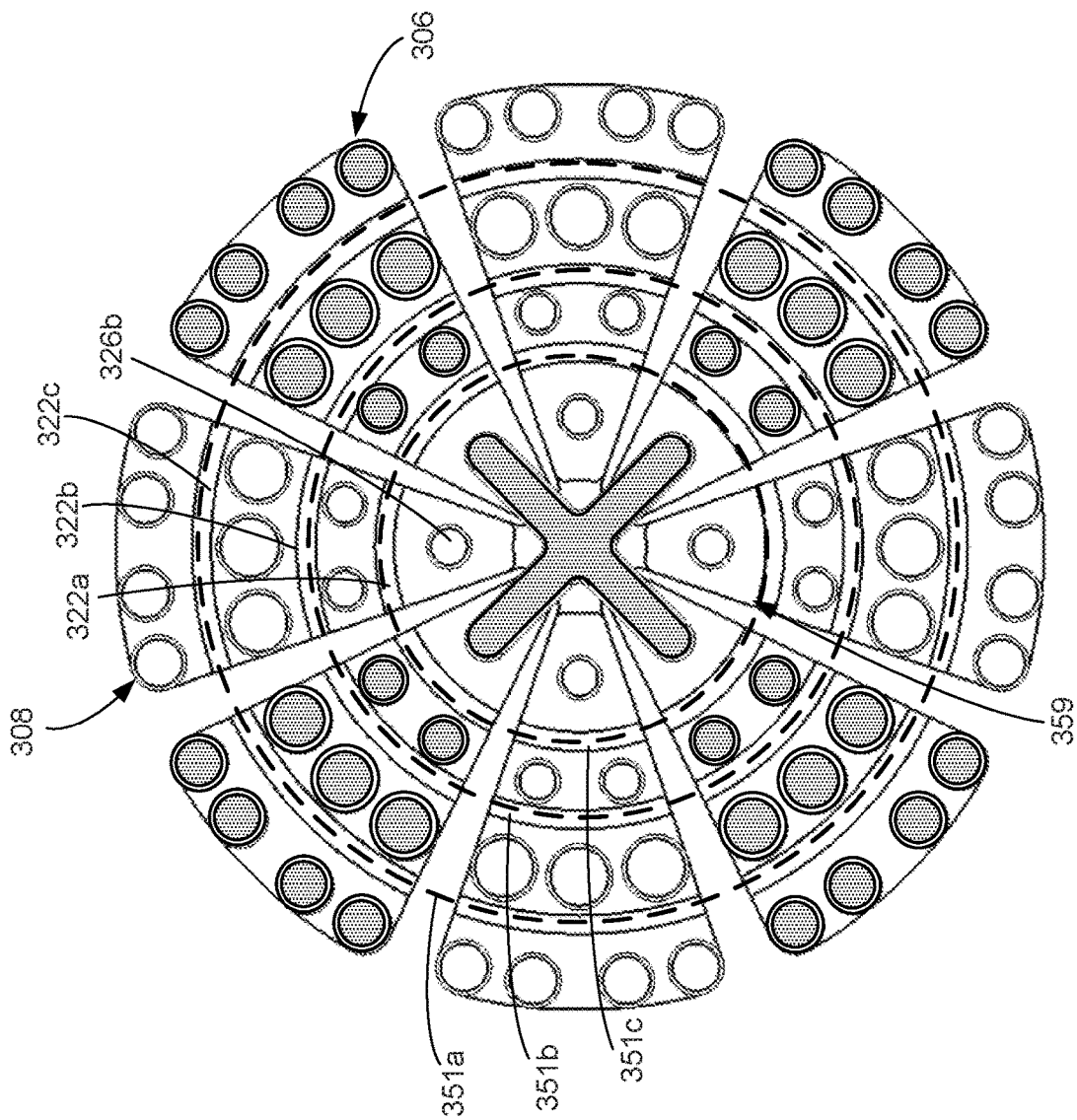
FIG. 9 is a bottom view of electrical conductors of the wetness sensing device of FIG. 8A.
Figure 10A:
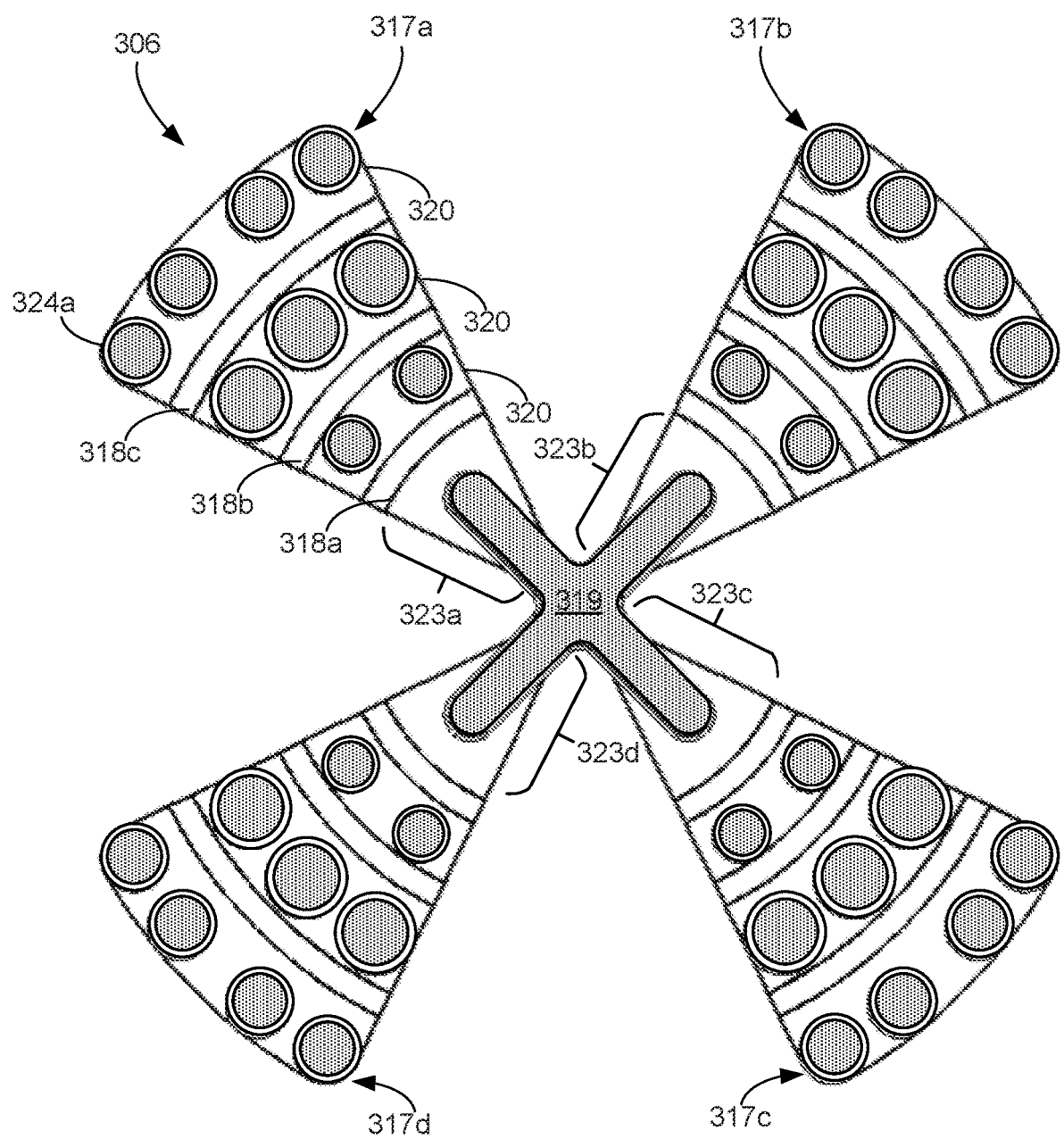
FIG. 10A is a bottom view of an electrical conductor of the wetness sensing device of FIG. 8A.
Figure 10B:
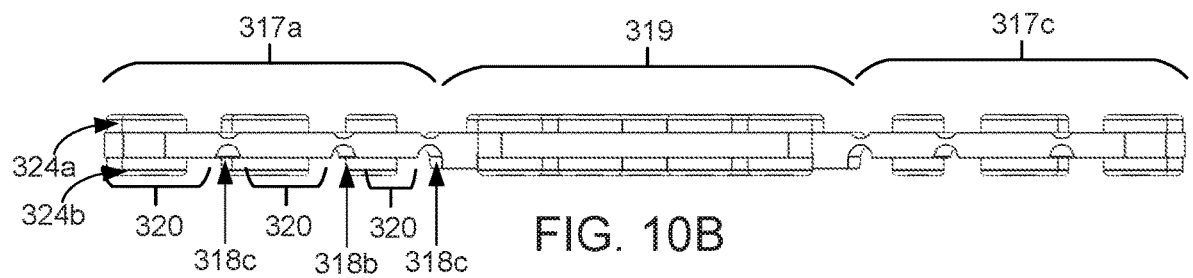
FIG. 10B is a side view of the electrical conductor of FIG. 10A.

Referring to FIG. 9, similar to the wetness sensing device 200, the wetness sensing device 300 includes a first electrical conductor 306 and a second electrical conductor 308. Referring to FIGS. 10A and 10B, the first electrical conductor 306 includes a central portion 319 and radially extending portions 317a-317d (collectively referred to as radially extending portions 217). The central portion 319 is, for example, cross-shaped and has a lobe 323a-323d attached to each of the radially extending portions 317a-317d.

Each of the radially extending portions 317a-317d extends radially outward from the central portion 319. The radially extending portions 317a-317d can be, for example, sectors of a circle defining an outer perimeter 312 (shown in FIG. 8C) of the wetness sensing device 300. A subtended angle of each sector can be, for example, between 30 and 60 degrees, e.g., between 30 and 50 degrees, between 35 degrees and 55 degrees, between 40 degrees and 60 degrees, etc.

While the following description is presented in reference to the radially extending portion 317a, the radially extending portions 317b-317d include features that are similar to or identical to the features of the radially extending portion 317a. In some examples, the first electrical conductor 306 is axisymmetric about the central axis Y3 such that the radially extending portions 317a-317d are identical to one another.

Hinge portions 318a-318c (collectively referred to as hinge portions 318) of the radially extending portion 317a enable deflection of the radially extending portions 317a relative to the central portion 319 of the first electrical conductor 306 as well as deflection within the radially extending portion 317a. The hinge portion 318a connects the radially extending portion 317a to the central portion and enables the radially extending portion 317a to deflect, e.g., in its entirety, relative to the central portion 319. The hinge portions 318b, 318c enable relative deflection of sections 320 of the radially extending portion 317a relative to adjacent sections 320.

Rather than extending linearly as the hinge portions 218 of the wetness sensing device 200 do, the hinge portions 318 extend along circles 351a-351c (shown in FIG. 9) that circumscribe the central portion 319, e.g., having centers aligned with the central axis Y3. The circle 351a, for example, can define the extent of the central portion 319 of the first electrical conductor 306 and the extent of a central portion 359 of the second electrical conductor 308. The hinge portions 318 extend along different arcs of these circles 351a-351c. The arcs for the hinge portions 318 have, in some cases, angles of curvature identical to the subtend angle of the sector defined by the radially extending portion 317a. In this regard, the hinge portions 318 further from the central axis Y3 have greater lengths than the hinge portions 318 close to the central axis Y3.

Figure 11:
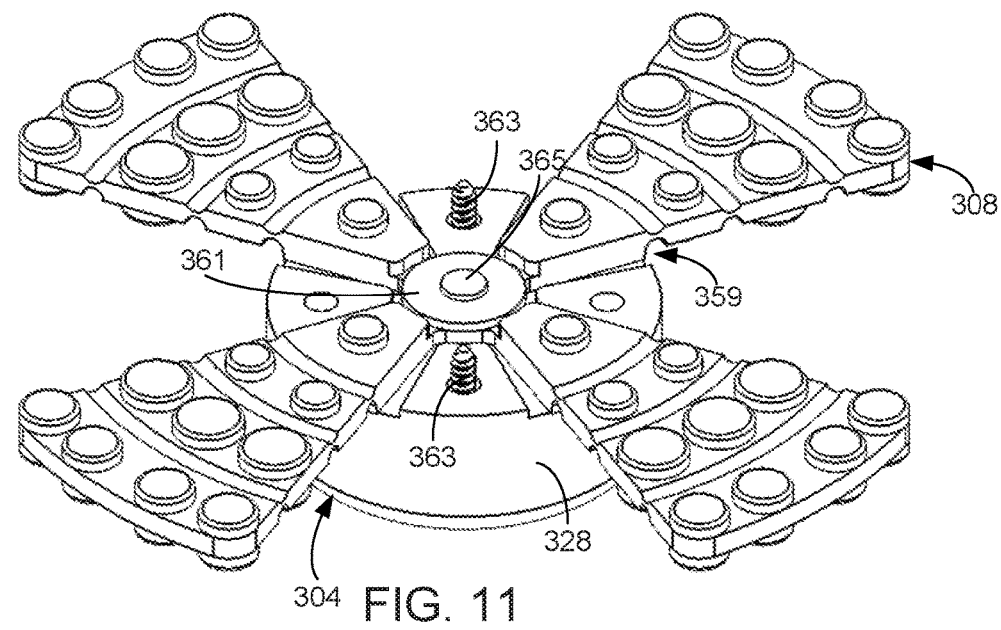
FIG. 11 is a bottom perspective view of the wetness sensing device of FIG. 8A with an electrical conductor and a cover removed.

Similar to the hinge portions 218 described with respect to the wetness sensing device 200, as shown in FIG. 11, the hinge portions 318 can include, for example, living hinges. The first electrical conductor 306 can be formed from a monolithic material that forms the central portion 319 and the radially extending portions 317a-317d. The material is similar to the material described for the hinge portions 218 of the wetness sensing device 200. The relative thicknesses of the hinge portions 318 and the sections 320 are similar to the relative thicknesses of the hinge portions 218 and the sections 220.

Similar to the bosses 224a, 224b of the first electrical conductor, referring to FIGS. 8A, 8B, 10A, and 10C, bosses 324a, 324b of the first electrical conductor 306 extend in directions parallel to the central axis Y3. The bosses 324a, 324b are only positioned within the radially extending portions 317a-317d and not the central portion 319. However, in some implementations, the central portion 319 includes bosses extending along the central axis Y3. Because the size of the sections 320 further from the central axis Y3 are larger than the size of the sections 320 close to the central axis Y3, the sections 320 further from the central axis Y3 have a greater number of bosses 324a, 324b than the sections 320 closer to the central axis Y3.

The second electrical conductor 308 is similar to the first electrical conductor 306 except that the central portion 359 of the second electrical conductor 308 includes bosses 326b within the central portion 359. The second electrical conductor 308 also includes other features, as described herein, that enables engagement between the first and second electrical conductors 306, 308. As shown in FIG. 9, hinge portions 322a-322c (collectively referred to as hinge portions 322) of the second electrical conductor 308 are positioned along the circles 351a-351c but along different arcs along the circles 351a-351c.

Rather than being interlocked with one another in the manner described with respect to the first and second electrical conductors 206, 208, as shown in FIG. 9, the first and second electrical conductors 306, 308 are both positioned at a central portion of the medical wetness sensing device 300, e.g., proximate the central axis X3 of the wetness sensing device 300. The central portion 359 of the second electrical conductor 308 overlies the central portion 319 of the first electrical conductor 306.

Referring to FIG. 11, an insulator 361 is positioned between the central portion 359 of the second electrical conductor 308 and the central portion 319 of the first electrical conductor 306 (shown in FIG. 9). The insulator 361 is a spacer that electrically isolates the electrical conductors 306, 308 from one another and inhibits electrical contact between the central portions 319, 359 of the electrical conductors 306, 308.

Figure 8B:
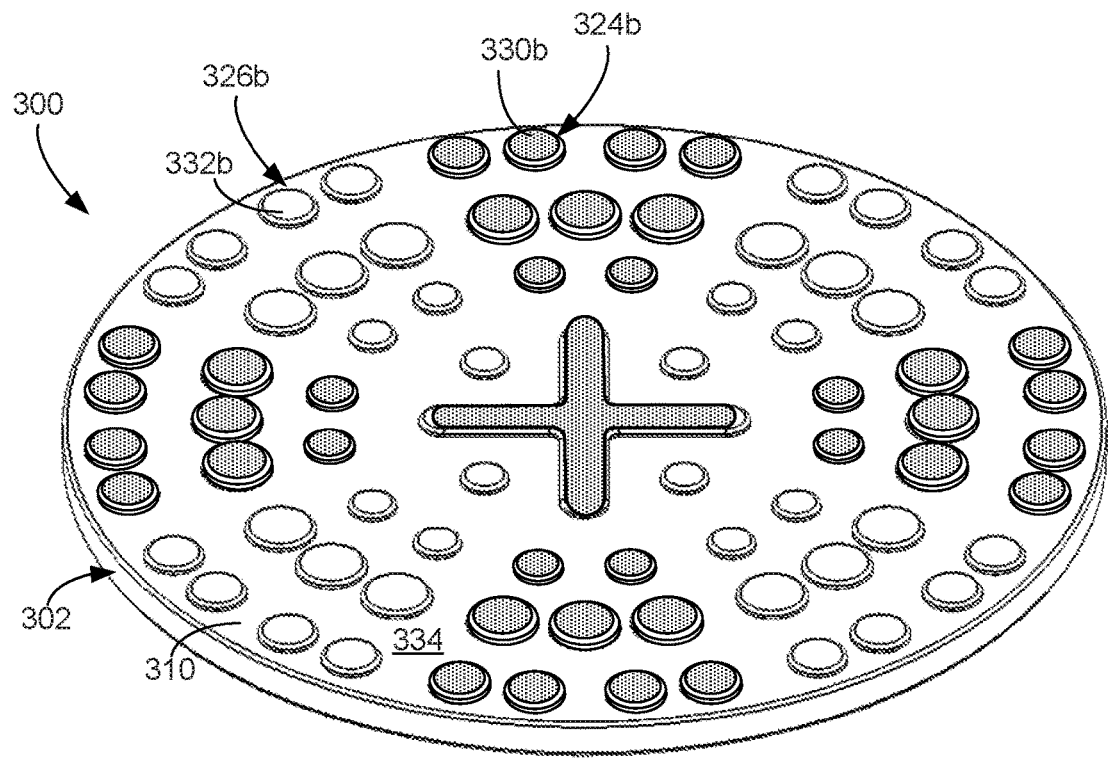
FIG. 8B is a bottom perspective view of the wetness sensing device of FIG. 8A.
Figure 8C:
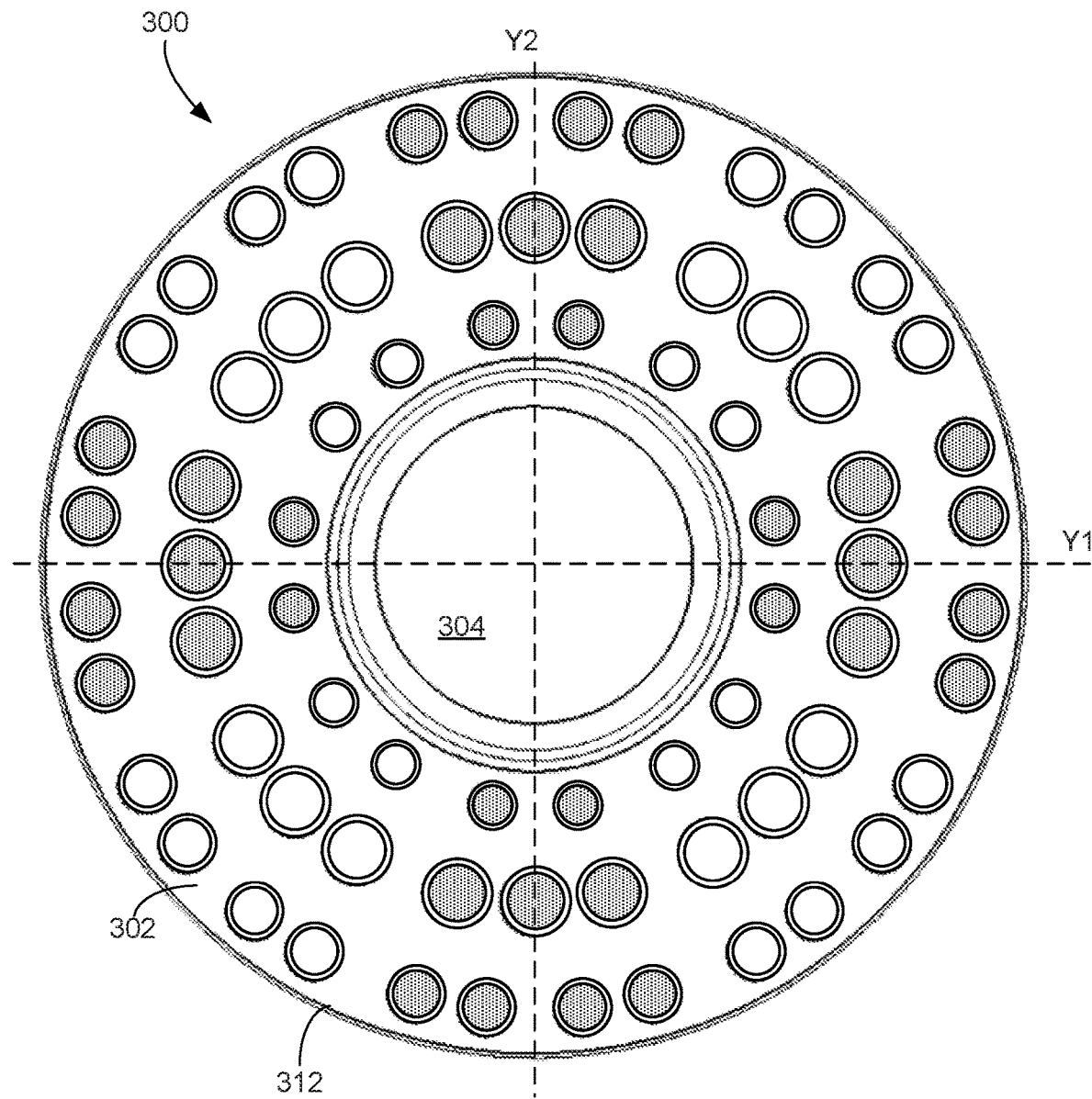
FIG. 8C is a top view of the wetness sensing device of FIG. 8A.

Referring back to FIG. 8B, the bosses 324b, 326b have end portions 330b, 332b defining an inner surface 334 of the base 302. Similar to the inner surface 234, the inner surface 334 is adapted to be disposed on the wearer of the wetness sensing device 300. As shown in FIGS. 8A and 8B, the bosses 324a, 324b, 326a, 326b are similar to the bosses 224a, 224b, 226a, 226b in that they have exposed end portions 330b, 332b on the inner surface 334 of the base 302 and outer surface 335 of the base 302. The inner surface 334 is placed and pressed against the wearer or against gauze over skin of the wearer, the base 302 of the wetness sensing device 300 deflects to conform to the skin and the venous needle and, despite uneven and sharp geometries that the combination of the wearer's skin and the venous needle generate, to remain secured to the wearer.

The other portions of the inner surface 334 and the outer surface 335 of the base 302 are defined by the cover 310, e.g., formed in a manner similar to the cover 210. The cover 310 extends across both top and bottom portions of the electrical conductors 306, 308. The first and second electrical conductors 306, 308 are exposed along the inner surface 334 of the wetness sensing device 300. In particular, the end portions of the bosses 324b, 326b extend through the cover 310 such that the bosses 324b, 326b are exposed on the inner surface 334 of the base 202 and thus may contact medical fluid during a treatment. In addition, the cross-shaped central portion 319 of the first electrical conductor 306 is exposed along the inner surface 334, while the bosses 326b of the central portion 359 of the second electrical conductor 308 are exposed along the inner surface 334.

The housing 304 is similar to the housing 204 and thus contains electronic components to facilitate detection of medical fluid contact with the electrical conductors 306, 308 of the wetness sensing device 300. The housing 304 thus contains control circuitry and engages the cover 310 to form the fluid tight seal to inhibit fluid from leaking into the housing 304.

In some implementations, as shown in FIG. 11, a lower housing portion 328 of the housing 304 is directly fastened to the first electrical conductor 306. Fasteners 363 are positioned to secure the lower housing portion 328 to the first electrical conductor 306. Other fasteners may be present to secure the lower housing portion 328 to the second electrical conductor 306. The fasteners 363 and the other fasteners can inhibit relative rotation and translation of between the first and second electrical conductors 306 and the housing 304. The second electrical conductor 308 is positioned between the first electrical conductor 306 and the lower housing portion 328. The lower housing portion 328 includes an alignment boss 365 that extends through a corresponding opening in the second electrical conduct 308 and engages with a corresponding bore (not shown) on the first electrical conductor 306. The alignment boss 365, when engaged with the first and second electrical conductors 306, 308, aligns the electrical conductors 306, 308 with the central axis Y3 of the wetness sensing device 300.

While the electrical conductors 306, 308 are described and shown as including four radially extending portions are shown, in some implementations, an electrical conductor includes fewer or more radially extending portions, e.g., at least three radially extending portions, at least four radially extending portions, etc.

Dialysis Systems

Figure 12:
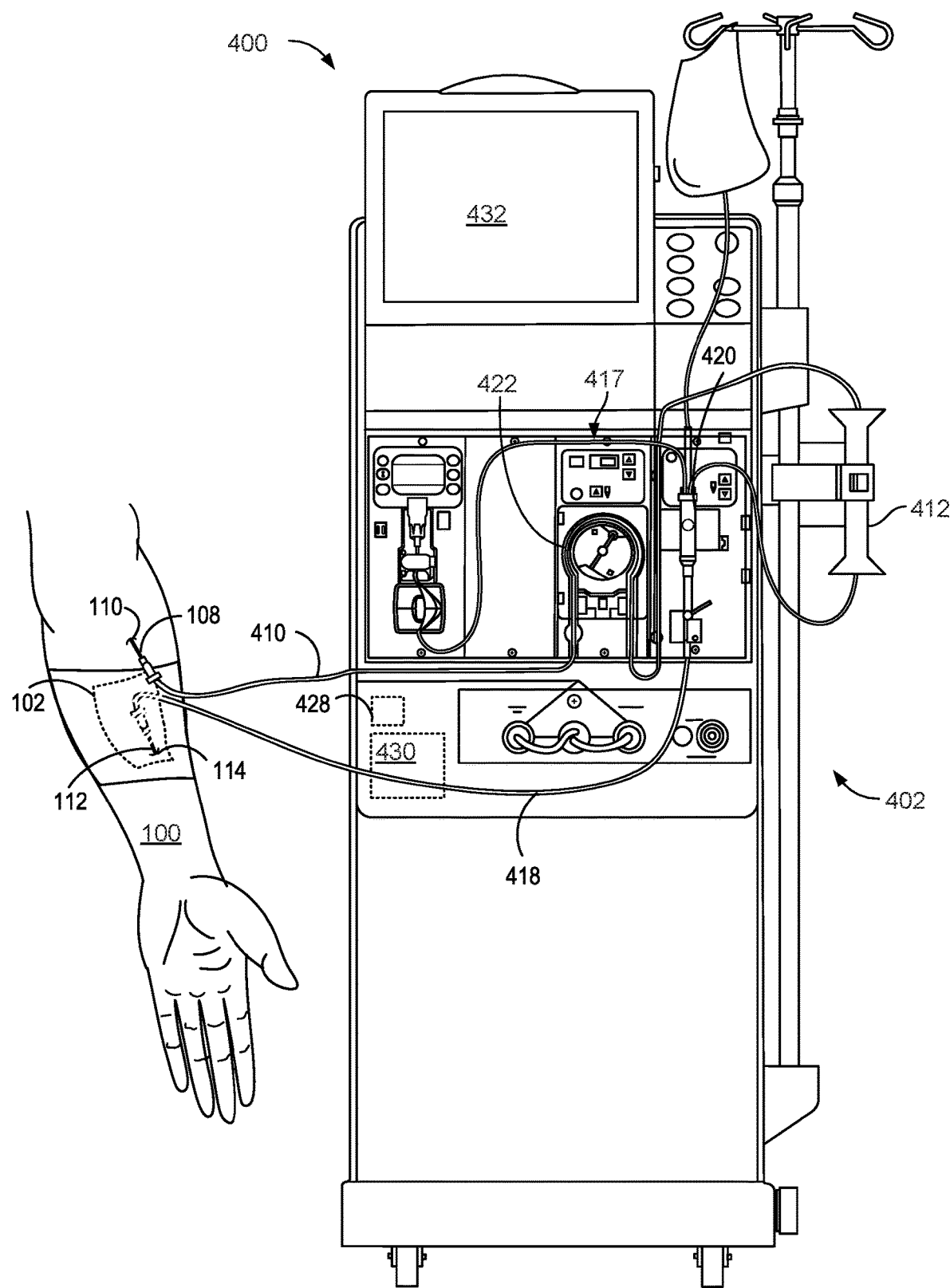
FIG. 12 is a front view of a dialysis system utilizing a wetness sensing device at a patient access.

The wetness sensing devices described herein (e.g., the wetness sensing device 200, the wetness sensing device 300) can be used with dialysis systems. As shown in FIG. 12, for example, a dialysis system 400 includes a dialysis machine 402 connected to the patient 100.

The arterial needle 108 inserted into the arterial access site 110 on the patient 100 connects the circulatory system of the patient 100 to the dialysis machine 402 to allow blood from the patient 100 to flow through an arterial line 410 to a dialyzer 412 of the dialysis machine 402. Dialysis solution (e.g., dialysate, salt solution) flows alongside the blood flowing through the dialyzer 412 to filter the blood. The venous needle 112 inserted into the venous access site 114 connects the dialyzer 412 to the circulatory system of the patient 100 to allow filtered blood to flow from the dialyzer 412 through a venous line set 417. The venous line set 417 includes a venous line 418 to conduct the filtered blood toward the patient and a drip chamber 420 to remove, for example, air, debris, clots, and other particulate matter from the filtered blood. A peristaltic pump 422 compresses portions of the arterial line 410 to generate a flow of the filtered blood through the arterial line 410 and the venous line set 417 so that blood can be circulated throughout the dialysis system 400.

The wetness sensing device 102 (which can be any of the wetness sensing devices described herein, e.g., the wetness sensing device 200 or the wetness sensing device 300) applied on the patient 100 in the vicinity of the venous access site 114 on top of the venous needle 112 detects blood leaks from the venous access site 114. In an absence of liquid (e.g., blood) contacting an inner surface of the wetness sensing device 102, the wetness sensing device 102 can operate in an idle state. In the idle state, a power source (e.g., the power source 120, the power source 242) can supply power to a circuit (e.g., the control circuitry 240) of the wetness sensing device 102 to generate electrical test signals that can detect a presence of blood. The electrical test signals may not indicate the presence of blood, and the wetness sensing device 102 can continue to periodically generate the electrical test signals to detect absence/presence of the blood.

When the electrical test signals indicate the presence of blood, the wetness sensing device 102 can communicate with the dialysis machine 402 to indicate to the dialysis machine 402 that a blood leak has occurred. The wetness sensing device 102 can include a wireless transceiver (e.g., the wireless transceiver of the control circuitry 240) that can transmit a wireless signal that a wireless transceiver 428 of the dialysis machine 402 can receive. The wireless signal can indicate that the wetness sensing device 102 has detected a presence of blood due to, e.g., blood leaking around the venous access site 114 from the venous needle 112. The wireless transceiver 428 can generate electrical signals in response to receiving the wireless signal.

A controller 430 of the dialysis machine 402 can receive and transmit electrical signals operable to and from systems of the dialysis machine 402. For example, the controller 430 can receive electrical signals from the wireless transceiver 428. The electrical signals can indicate that the wetness sensing device 102 has detected the presence of blood. Based on the electrical signals, the controller 430 can modify operations of components of the dialysis machine 402, such as a pump speed of the peristaltic pump 422, a display 432 of the dialysis machine 402, and other electrical and electromechanical systems.

Methods of Use

A method of using a wetness sensing device (e.g., the wetness sensing device 200, the wetness sensing device 300, or other wetness sensing device described herein) during a dialysis treatment of a patient is described herein.

An operator (e.g., a patient, a physician, a nurse, a medical practitioner) punctures an access site on skin of the patient to access a corporeal blood circuit of the patient. Before initiating the dialysis treatment, now also referring to FIGS. 1A, 1B, and 12, the operator can disinfect and clean skin of the patient 100 and then insert the arterial needle 108 into the arterial access site 110 and the venous needle 112 into the venous access site 114. The operator can thus use the arterial needle 108 and the venous needle 112 to puncture the respective access sites 110, 114 on the skin of the patient to access the circulatory system of the patient 100. The arterial needle 108 and the venous needle 112, when inserted, place the circulatory system of the patient 100 in fluid communication with the dialysis machine 402.

As shown in FIGS. 1A and 12, after inserting the arterial needle 108 and the venous needle 112, the operator places the wetness sensing device 102 over the skin of the patient 100 in the vicinity of the venous access site 114. In some cases, the gauze 105, as shown in FIG. 1B, is placed over the needle, and then the wetness sensing device 102 is placed over the gauze 105. The operator can, for example, firmly place the inner surface of the wetness sensing device 102 against the gauze 105 and against the venous access site 114 such that the inner surface of the wetness sensing device 102 conforms to the venous access site 114. In the event of a blood leak from the patient 100, the gauze 105 absorbs the blood, the wetness sensing device 102 detects the blood through the gauze 105. The flexibility of the wetness sensing device 102 allows the inner surface of the wetness sensing device 102 to conform to the gauze 105, which in turn conforms to the skin. The inner surface of the wetness sensing device 102 is able to maintain contact with the gauze 105 and thus easily detect any blood that leaks onto the gauze 105. The wetness sensing device 102 can detect blood that leaks from the venous access site 114 in the event of, for example, dislodgement of the venous needle 112.

Figure 13:
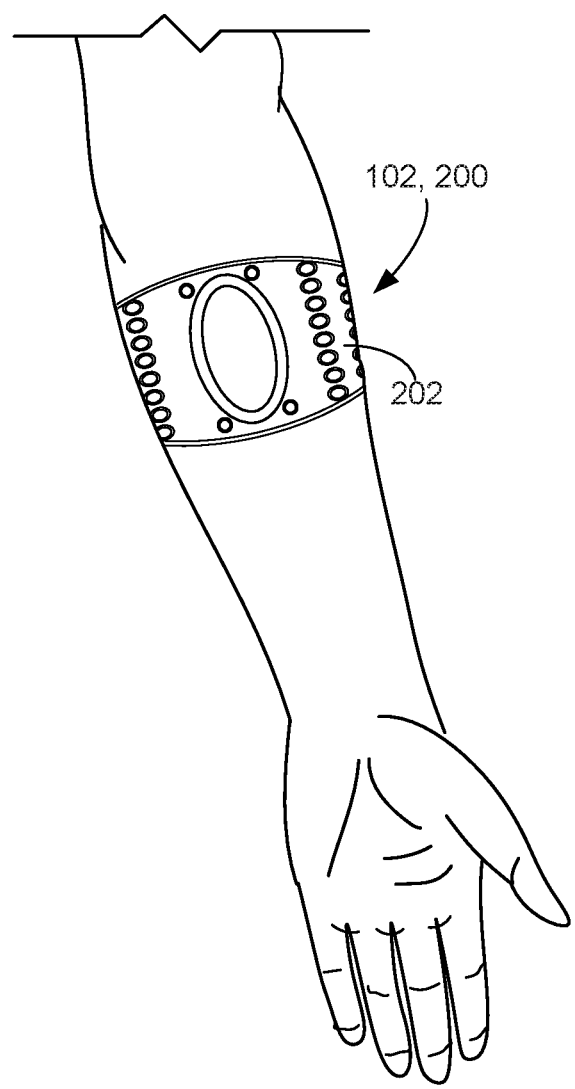
FIG. 13 illustrates the wetness sensing device of FIG. 2A wrapped around an arm of a patient.
Figure 14:
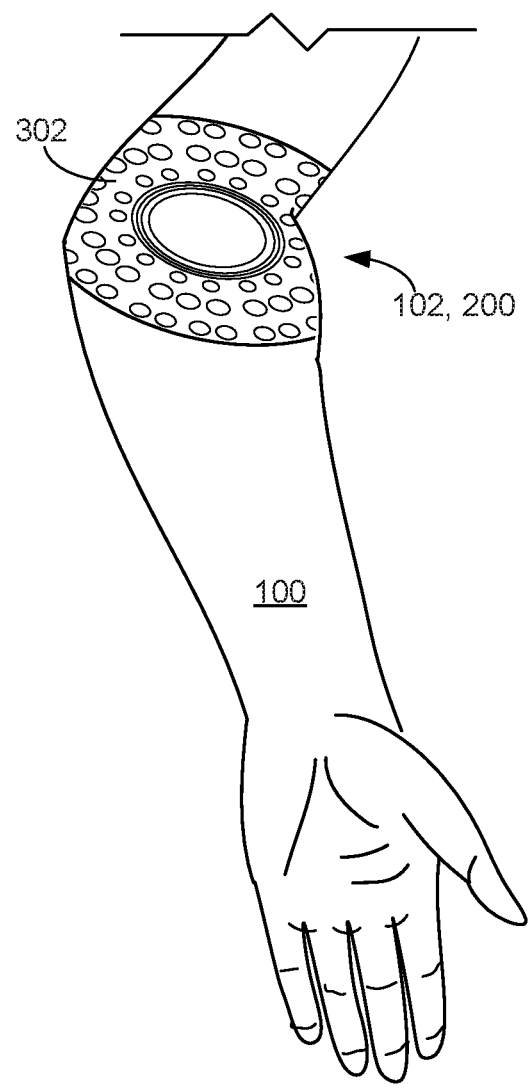
FIG. 14 illustrates the wetness sensing device of FIG. 8A wrapped around an arm of a patient.

As shown in FIG. 13 in which the wetness sensing device 102 corresponds to the wetness sensing device 200, the wetness sensing device 200 is disposed on the patient 100 such that the base 202 of the wetness sensing device 200 bends along the contours of the patient 100. Similarly, as shown in FIG. 14 in which the wetness sensing device 102 corresponds to the wetness sensing device 300, the wetness sensing device 300 is disposed on the patient such that the base 302 of the wetness sensing device 300 bends along the contours of the patient 100. The hinge portions of the wetness sensing devices 200, 300 described herein enable the bending of the bases.

Referring back to FIGS. 1A, 1B, and 12, to secure the wetness sensing device 102 to the skin surrounding the venous access site 114, the operator can apply the cloth 116 around the gauze 105 and the wetness sensing device 102 to secure the wetness sensing device 102 against the skin or the gauze 105. The operator can wrap the cloth 116 around an arm of the patient 100 such that the inner surface of the wetness sensing device 102 is pressed against the venous access site 114, the skin of the patient 100, and the venous needle 112. The wetness sensing device 102 can seal the inner surface of the wetness sensing device 102 from an outside environment such that blood leaking from the venous access site 114 remains sealed between the inner surface and the skin of the patient 100. As described herein, during use of the wetness sensing device 102, the flexibility of the wetness sensing device 102 can enable the wetness sensing device 102 to conform to the skin and the venous needle 112, thus improving the reliability of the wetness sensing device 102 to detect blood leaks.

The operator can initiate the dialysis treatment on the dialysis machine 402. Before initiating the dialysis treatment, the operator can further set various dialysis treatment parameters of the dialysis machine 402. When the operator initiates the dialysis treatment, the peristaltic pump 422 of the dialysis machine 402 circulates the blood from the patient 100 through the dialyzer 412 to clean and filter the blood. Blood can travel along the venous line set 417 from the patient 100 through the arterial needle 108 to the dialyzer 412. After the dialyzer 412 filters the blood, filtered blood can exit the dialyzer 412 and travels along the venous line set 417 through the venous needle 112 back to the patient 100. Within the dialyzer 412, alongside the flowing blood, a dialysis solution that can include salts, buffers, and/or acids can remove toxins from the blood.

During treatment, if a blood leak occurs around the venous access site 114, the blood can cause the wetness sensing device 102 to generate a wireless signal in response to the presence of the blood, as described herein. The blood can contact an inner surface of the wetness sensing device 102 and then generate an electrically conductive path that would otherwise not be present in the absence of the blood. The wireless transceiver 428 of the dialysis machine 402 can receive the wireless signal and transmit a corresponding electrical signal to the controller 430 of the dialysis machine 402. In response to the electrical signal, the controller 430 can control various operations of the dialysis machine 402. For example, the controller 430 can adjust the pump speed of the peristaltic pump 422, turn off the peristaltic pump 422, activate an audible alarm through a speaker, and/or display an error message on the display 432 of the dialysis machine.

In response to changes in operation of the dialysis machine 402 (e.g., by triggering the alarm, by issuing an error message, or altering an operation of the peristaltic pump 422), the operator can modify the course of treatment to resolve the blood leak. The operator can replace a component of the dialysis machine 402, such as, for example, the venous needle 112, the wetness sensing device 102, or the venous line set 417. In some cases, dislodgement of the venous needle 112 may have caused the blood leak, and the operator can simply adjust how the venous needle 112 is inserted into the patient 100 (e.g., a depth of penetration of the venous needle 112, an angle of penetration of the venous needle 42).

In the absence of blood, the control circuitry 240 may operate the wetness sensing device 102 in an idle state in which the controller monitors the wetness sensing device 102 to determine if the wetness sensing device 102 is detecting a presence/absence of blood. For example, the controller can periodically transmit electrical test signals that determine whether a closed electrical loop has been formed between different electrical conductors of the wetness sensing device 102, as described herein.

After completion of the dialysis treatment, the operator can remove and dispose of the wetness sensing device 102. The operator can then disconnect the arterial needle 108 and the venous needle 112 from the patient 100 and dispose of the venous line set 417.

Alternative Implementations

The examples described herein can be implemented in a variety of ways without departing from the scope of the specification.

The examples of using wetness sensing devices described with respect to FIGS. 11 and 13 are directed to a dialysis treatment, though, in other implementations, the wetness sensing devices can be used for other appropriate medical treatments. As described herein, the wetness sensing devices can be used for medical procedures requiring access to the circulatory of the patient, such as cardiopulmonary bypass procedures, apheresis procedures, etc.

While the hinge portions 218, 222, 318, 322 are described as being integral to the electrical conductors, in some implementations, the hinge portions 218, 222, 318, 322 each include a movable joint mechanism connecting adjacent sections of the electrical conductors. In some implementations, the movable joint mechanism includes a living hinge as described herein or rigid hinges enabling relative rotation of the adjacent sections of the electrical conductors. For example, rather than deforming to enable relative rotation of adjacent sections, the hinge portions 218, 222 include a bearing about which adjacent sections pivot.

The wetness sensing devices can additionally be used to detect liquids other than blood. These liquids can be removed or introduced to a patient. For example, the wetness sensing devices can be used to detect peritoneal dialysis fluid during a peritoneal dialysis treatment. The wetness sensing devices alternatively can be used to detect hemodialysis fluid during a hemodialysis treatment. In another example, the wetness sensing devices can be used during a diabetes treatment and can detect presence of insulin. The wetness sensing devices can be used during intravenous fluid delivery to detect water, saline, or other solutions. The wetness sensing devices can be use during drug delivery and other appropriate treatments in which liquid is transferred to and from the patient.

The wetness sensing devices (e.g., the wetness sensing device 102) have been described to be placed above the venous access site (e.g., the venous access site 114). Additionally or alternatively, the wetness sensing devices can be placed on top an arterial access site to detect blood leaking as the blood travels away from the patient.

The control circuitry 240 determines whether continuity exists between separated electrical conductors 206, 208, 306, 308 to detect presence of liquid on the inner surface of the wetness sensing device 200, 300. Electricity continuity has been described to be indicated by a resistance below a threshold resistance for the electrical path that the electrical test signal takes along the electrical conductors 206, 208, 306, 308. The threshold resistance can vary depending on the conductivities of the cover or other insulative portions of the wetness sensing device. In addition, the threshold resistance can vary depending on the conductivities of the electrical conductors of various implementations of wetness sensing devices described herein.

In some examples, electrical systems of a wetness sensing device may detect changes in appropriate characteristics that can change in presence of liquid such as blood. The electrical systems may interpret a change in capacitance, current, voltage, or other appropriate electrical parameter as indicative of presence of liquid.

Patterns of exposed portions of the electrical conductors 206, 208, 306, 308 along the inner surfaces of the wetness sensing devices 200, 300 can be modified. The appropriate pattern to utilize may be determined based upon manufacturing characteristics such as cost and feasibility. In some cases, the wetness sensing devices include partitions that include separated sections that each independently detect liquid. The overall conductive pattern may comprise multiple sections each including electrical conductors. The sections, in the presence and absence of blood alike, do not include an electrically continuous path between the sections. The sections and patterns may be arranged in any manner known in the art. For example, the inner surfaces of wetness sensing devices can be divided into quadrants, which can allow the wetness sensing devices to further determine a location, among four quadrants of the inner surface, where blood is detected.

The wetness sensing devices and the dialysis machine include wireless transceivers. In some cases, the wetness sensing devices can include wireless transmitters and the dialysis machine can include a wireless receiver. When the wetness sensing devices transmit wireless signals over the wireless transmitters, the microcontroller of the wetness sensing devices can disable transmission of the wireless signals after a predetermined period of time, such as, for example, 1 to 10 minutes.

Elements of different implementations described herein may be combined to form other implementations not specifically set forth above. Elements may be left out of the structures described herein without adversely affecting their operation. Furthermore, various separate elements may be combined into one or more individual elements to perform the functions described herein.

Various embodiments discussed herein may be combined with each other in appropriate combinations in connection with the system described herein. Additionally, in some instances, the order of steps in a method may be modified, where appropriate. Further, various aspects of the systems described herein may be implemented using software, hardware, a combination of software and hardware and/or other computer-implemented modules or devices having the described features and performing the described functions.

Software implementations of aspects of the system described herein may include executable code that is stored in a computer-readable medium and executed by one or more processors. The computer-readable medium may include volatile memory and/or non-volatile memory, and may include, for example, a computer hard drive, ROM, RAM, flash memory, portable computer storage media such as a CD-ROM, a DVD-ROM, a flash drive and/or other drive with, for example, a universal serial bus (USB) interface, and/or any other appropriate tangible or non-transitory computer-readable medium or computer memory on which executable code may be stored and executed by a processor. The system described herein may be used in connection with any appropriate operating system.

A number of implementations have been described. Nevertheless, it will be understood that various modifications may be made. Accordingly, other implementations are within the scope of the claims.

What is claimed is:

1. A medical wetness sensing device comprising:
a base adapted to be disposed on a wearer of the medical wetness sensing device, wherein the base comprises
a first electrical conductor comprising a first longitudinally extending segment, a second longitudinally extending segment, and a transversely extending segment connecting the first longitudinally extending segment to the second longitudinally extending segment, wherein at least one of the first longitudinally extending segment or the second longitudinally extending segment extends from a first half into a second half of the medical wetness sensing device, the first half and the second half being defined by a longitudinal axis of the medical wetness sensing device, wherein the first electrical conductor comprises bosses having end portions, and
a second electrical conductor electrically insulated from the first electrical conductor, wherein the second electrical conductor comprises bosses having end portions, and wherein the end portions of the bosses of the first electrical conductor and the end portions of the bosses of the second electrical conductor define a surface of the base to be disposed on the wearer; and
a controller electrically connected to the first electrical conductor and the second electrical conductor, the controller configured to detect a presence or an absence of a medical fluid electrically connecting the first and second electrical conductors.

2. The medical wetness sensing device of claim 1, wherein the first electrical conductor is interlocked with the second electrical conductor.

3. The medical wetness sensing device of claim 1, wherein the first electrical conductor comprises a hinge portion enabling a first portion of the first electrical conductor to deflect, at the hinge portion, relative to a second portion of the first electrical conductor.

4. The medical wetness sensing device of claim 3, wherein:
the second electrical conductor comprises a hinge portion enabling a first portion of the second electrical conductor to deflect, at the hinge portion of the second electrical conductor, relative to a second portion of the second electrical conductor, and
the hinge portion of the first electrical conductor and the hinge portion of the second electrical conductor are collinear.

5. The medical wetness sensing device of claim 3, wherein the hinge portion of the first electrical conductor comprises a living hinge.

6. The medical wetness sensing device of claim 3, wherein the hinge portion of the first electrical conductor has a thickness at most one-half of a maximum thickness of the first electrical conductor.

7. The medical wetness sensing device of claim 3, wherein the hinge portion is a first hinge portion, and the first electrical conductor further comprises a second hinge portion enabling the second portion of the first electrical conductor to deflect, at the second hinge portion, relative to a third portion of the first electrical conductor.

8. The medical wetness sensing device of claim 3, wherein the first portion of the first electrical conductor comprises the first longitudinally extending segment, and the second portion of the first electrical conductor comprises the second longitudinally extending segment.

9. The medical wetness sensing device of claim 3, wherein the transversely extending segment comprises the hinge portion.

10. The medical wetness sensing device of claim 1, wherein the first longitudinally extending segment extends from the first half into the second half, and
wherein the second longitudinally extending segment extends only within the first half.

11. The medical wetness sensing device of claim 1, wherein the transversely extending segment is a first transversely extending segment, and the first electrical conductor comprises:
at least three longitudinally extending segments comprising the first longitudinally extending segment and the second longitudinally extending segment, and
at least two transversely extending segments comprising the first transversely extending segment.

12. The medical wetness sensing device of claim 11, wherein the at least three longitudinally extending segments comprises a third longitudinally extending segment, and the at least two transversely extending segments comprises a second transversely extending segment connecting the second longitudinally extending segment to the third longitudinally extending segment.

13. The medical wetness sensing device of claim 12, wherein the second longitudinally extending segment is fixed to the third longitudinally extending segment by the second transversely extending segment.

14. The medical wetness sensing device of claim 12, wherein the second longitudinally extending segment is deflectable relative to the third longitudinally extending segment.

15. The medical wetness sensing device of claim 1, further comprising:
a housing coupled to the bosses of the first electrical conductor and the second electrical conductor to separate the first electrical conductor from the second electrical conductor.

16. The medical wetness sensing device of claim 1, wherein the first and second electrical conductors comprise a rigid polymeric material.

17. The medical wetness sensing device of claim 16, wherein the rigid polymeric material has an elastic modulus between 0.1 and 5 GPa.

18. The medical wetness sensing device of claim 1, wherein the first electrical conductor is formed from a polymer loaded with conductive materials.

19. The medical wetness sensing device of claim 1, wherein the base comprises a cover covering at least a portion of the first electrical conductor and at least a portion of the second electrical conductor.

20. The medical wetness sensing device of claim 19, further comprising a housing within which the controller is contained, the housing engaging the cover to form a fluid tight seal that inhibits entry of fluid into an interior of the housing.

21. The medical wetness sensing device of claim 19, wherein:
   the cover defines multiple portions of the first electrical conductor that are exposed on a surface of the base to be disposed on the wearer and multiple portions of the second electrical conductor that are exposed on the surface, and
   the controller is configured to detect the presence of the medical fluid when at least one of the multiple portions of the first electrical conductor and at least one of the multiple portions are electrically connected by the medical fluid.

22. The medical wetness sensing device of claim 19, wherein the cover comprises an elastomeric material.

23. The medical wetness sensing device of claim 1, further comprising a wireless transmitter.

24. A dialysis system, comprising:
   a dialysis machine comprising a wireless receiver;
   a medical wetness sensing device comprising
      a base comprising first and second electrical conductors configured to be electrically connected to one another when a medical fluid is present on a surface of the base to be disposed on a wearer of the medical wetness sensing device, the first electrical conductor comprising a first longitudinally extending segment, a second longitudinally extending segment, and a transversely extending segment connecting the first longitudinally extending segment to the second longitudinally extending segment, wherein at least one of the first longitudinally extending segment or the second longitudinally extending segment extends from a first half into a second half of the medical wetness sensing device, the first half and the second half being defined by a longitudinal axis of the medical wetness sensing device, wherein the first electrical conductor comprises bosses having end portions, the second electrical conductor comprises bosses having end portions, and the end portions of the bosses of the first electrical conductor and the end portions of the bosses of the second electrical conductor define a surface of the base to be disposed on the wearer, and
      a controller to generate a signal indicating a presence or an absence of the medical fluid on the surface; and
   a wireless transmitter configured to transmit the signal to the wireless receiver.

25. The dialysis system of claim 24, wherein the dialysis machine is a hemodialysis machine.

26. The dialysis system of claim 24, wherein the medical wetness sensing device comprises the wireless transmitter.

* * * * *